United States Patent
Podsiadlo et al.

(10) Patent No.: US 10,047,304 B2
(45) Date of Patent: Aug. 14, 2018

(54) AROMATIC HYDROGENATION CATALYSTS AND USES THEREOF

(71) Applicants: Paul Podsiadlo, Easton, PA (US); Quanchang Li, Dayton, NJ (US); David Charles Calabro, Bridgewater, NJ (US); Jean Willem Lodewijk Beeckman, Columbia, MD (US); Lei Zhang, Basking Ridge, NJ (US); Kiara M. Benitez, Budd Lake, NJ (US); Matthew Scott Ide, Raritan, NJ (US); Stephen John McCarthy, Center Valley, PA (US); Mobae Afeworki, Phillipsburg, NJ (US); Simon Christopher Weston, Annandale, NJ (US); Preeti Kamakoti, Summit, NJ (US); Matu J. Shah, Hackettstown, NJ (US); Wenyih Frank Lai, Bridgewater, NJ (US); Meghan Nines, Lansdale, PA (US); David A. Griffin, Phillipsburg, NJ (US); Ivy D. Johnson, Lawrenceville, NJ (US)

(72) Inventors: Paul Podsiadlo, Easton, PA (US); Quanchang Li, Dayton, NJ (US); David Charles Calabro, Bridgewater, NJ (US); Jean Willem Lodewijk Beeckman, Columbia, MD (US); Lei Zhang, Basking Ridge, NJ (US); Kiara M. Benitez, Budd Lake, NJ (US); Matthew Scott Ide, Raritan, NJ (US); Stephen John McCarthy, Center Valley, PA (US); Mobae Afeworki, Phillipsburg, NJ (US); Simon Christopher Weston, Annandale, NJ (US); Preeti Kamakoti, Summit, NJ (US); Matu J. Shah, Hackettstown, NJ (US); Wenyih Frank Lai, Bridgewater, NJ (US); Meghan Nines, Lansdale, PA (US); David A. Griffin, Phillipsburg, NJ (US); Ivy D. Johnson, Lawrenceville, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 205 days.

(21) Appl. No.: 14/966,071

(22) Filed: Dec. 11, 2015

(65) Prior Publication Data
US 2016/0167032 A1 Jun. 16, 2016

Related U.S. Application Data

(60) Provisional application No. 62/091,071, filed on Dec. 12, 2014, provisional application No. 62/091,077, filed on Dec. 12, 2014.

(51) Int. Cl.
*C10G 45/52* (2006.01)
*B01D 15/00* (2006.01)
(Continued)

(52) U.S. Cl.
CPC ............ *C10G 45/52* (2013.01); *B01D 15/00* (2013.01); *B01D 53/02* (2013.01); *B01D 53/04* (2013.01); *B01D 53/047* (2013.01); *B01D 53/0462* (2013.01); *B01D 67/0088* (2013.01); *B01D 69/10* (2013.01); *B01D 71/70* (2013.01); *B01J 20/0229* (2013.01); *B01J 20/0237* (2013.01); *B01J 20/06* (2013.01); *B01J 20/08* (2013.01); *B01J 20/10* (2013.01); *B01J 20/103* (2013.01); *B01J 20/16* (2013.01); *B01J 20/18* (2013.01); *B01J 20/22* (2013.01); *B01J 20/262* (2013.01);
(Continued)

(58) Field of Classification Search
CPC ......... C10G 45/44; C10G 45/46; C10G 45/52
See application file for complete search history.

(56) References Cited

U.S. PATENT DOCUMENTS

| 3,178,392 A | 4/1965 | Kriner |
| 4,218,308 A | 8/1980 | Itoh et al. |

(Continued)

FOREIGN PATENT DOCUMENTS

| CN | 101804335 A | 8/2010 |
| CN | 101980013 A | 2/2011 |

(Continued)

OTHER PUBLICATIONS

Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.

(Continued)

*Primary Examiner* — Renee Robinson
(74) *Attorney, Agent, or Firm* — Lisa K. Holthus

(57) ABSTRACT

Hydrogenation catalysts for aromatic hydrogenation including an organosilica material support, which is a polymer comprising independent units of a monomer of Formula $[Z^1OZ^2OSiCH_2]_3$ (I), wherein each $Z^1$ and $Z^2$ independently represent a hydrogen atom, a $C_1$-$C_4$ alkyl group or a bond to a silicon atom of another monomer; and at least one catalyst metal are provided herein. Methods of making the hydrogenation catalysts and processes of using, e.g., aromatic hydrogenation, the hydrogenation catalyst are also provided herein.

25 Claims, No Drawings

(51) Int. Cl.

| | | |
|---|---|---|
| B01J 20/06 | (2006.01) | |
| B01J 20/08 | (2006.01) | |
| B01J 20/10 | (2006.01) | |
| B01J 20/18 | (2006.01) | |
| B01J 20/26 | (2006.01) | |
| B01D 53/04 | (2006.01) | |
| B01J 20/28 | (2006.01) | |
| B01J 20/286 | (2006.01) | |
| B01J 20/30 | (2006.01) | |
| B01J 20/32 | (2006.01) | |
| B01J 29/03 | (2006.01) | |
| C01B 37/00 | (2006.01) | |
| C08F 36/04 | (2006.01) | |
| C08F 36/20 | (2006.01) | |
| C08G 77/60 | (2006.01) | |
| C08F 2/00 | (2006.01) | |
| C08F 2/42 | (2006.01) | |
| C10G 25/00 | (2006.01) | |
| C10G 45/44 | (2006.01) | |
| B01J 20/02 | (2006.01) | |
| B01J 20/16 | (2006.01) | |
| B01D 53/02 | (2006.01) | |
| B01D 53/047 | (2006.01) | |
| B01J 23/44 | (2006.01) | |
| B01J 31/02 | (2006.01) | |
| B01J 37/02 | (2006.01) | |
| B01J 20/22 | (2006.01) | |
| B01J 35/10 | (2006.01) | |
| C07F 7/08 | (2006.01) | |
| C08G 77/26 | (2006.01) | |
| C10M 101/02 | (2006.01) | |
| B01D 67/00 | (2006.01) | |
| B01D 69/10 | (2006.01) | |
| B01D 71/70 | (2006.01) | |
| C10G 31/09 | (2006.01) | |
| C23C 16/56 | (2006.01) | |
| C08F 2/10 | (2006.01) | |
| C08F 4/659 | (2006.01) | |
| C08F 4/6592 | (2006.01) | |

(52) U.S. Cl.
CPC ........... *B01J 20/264* (2013.01); *B01J 20/286* (2013.01); *B01J 20/28011* (2013.01); *B01J 20/28057* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28073* (2013.01); *B01J 20/28076* (2013.01); *B01J 20/28078* (2013.01); *B01J 20/28083* (2013.01); *B01J 20/3042* (2013.01); *B01J 20/3204* (2013.01); *B01J 20/3212* (2013.01); *B01J 20/3236* (2013.01); *B01J 20/3238* (2013.01); *B01J 20/3272* (2013.01); *B01J 23/44* (2013.01); *B01J 29/0308* (2013.01); *B01J 31/0274* (2013.01); *B01J 35/1019* (2013.01); *B01J 35/1023* (2013.01); *B01J 35/1028* (2013.01); *B01J 35/1061* (2013.01); *B01J 37/0213* (2013.01); *B01J 37/0236* (2013.01); *C01B 37/00* (2013.01); *C07F 7/0807* (2013.01); *C07F 7/0818* (2013.01); *C08F 2/00* (2013.01); *C08F 2/42* (2013.01); *C08F 36/04* (2013.01); *C08F 36/20* (2013.01); *C08G 77/26* (2013.01); *C08G 77/60* (2013.01); *C10G 25/003* (2013.01); *C10G 31/09* (2013.01); *C10G 45/44* (2013.01); *C10M 101/02* (2013.01); *C23C 16/56* (2013.01); *B01D 2253/20* (2013.01); *B01D 2253/25* (2013.01); *B01D 2256/245* (2013.01); *B01D 2257/302* (2013.01); *B01D 2257/304* (2013.01); *B01D 2257/40* (2013.01); *B01D 2257/504* (2013.01); *B01D 2257/80* (2013.01); *B01J 2220/86* (2013.01); *C08F 4/659* (2013.01); *C08F 4/65912* (2013.01); *C08F 4/65916* (2013.01); *C08F 4/65925* (2013.01); *C08F 4/65927* (2013.01)

(56) References Cited

U.S. PATENT DOCUMENTS

| | | | |
|---|---|---|---|
| 5,630,937 | A | 5/1997 | Betz et al. |
| 5,719,322 | A | 2/1998 | Lansbarkis et al. |
| 7,300,905 | B2 | 11/2007 | Keefer et al. |
| 7,497,965 | B2 | 3/2009 | Wariishi et al. |
| 7,538,065 | B2 | 5/2009 | McCarthy et al. |
| 7,682,502 | B2 | 3/2010 | McCarthy et al. |
| 7,705,062 | B2 | 4/2010 | Markowitz et al. |
| 7,754,330 | B2 | 7/2010 | Hamada et al. |
| 7,767,620 | B2 | 8/2010 | Whitnall et al. |
| 7,947,799 | B2 | 5/2011 | Landskron et al. |
| 8,110,692 | B2 | 2/2012 | Bellussi et al. |
| 8,211,498 | B2 | 7/2012 | Ku et al. |
| 8,277,600 | B2 | 10/2012 | Hamada et al. |
| 8,277,661 | B2 | 10/2012 | Sah et al. |
| 8,425,762 | B2 | 4/2013 | McCarthy et al. |
| 8,441,006 | B2 | 5/2013 | Mchalak et al. |
| 8,470,074 | B2 | 6/2013 | Baugh et al. |
| 8,545,694 | B2 | 10/2013 | McCarthy et al. |
| 8,562,856 | B2 | 10/2013 | Giannantonio et al. |
| 8,568,520 | B2 | 10/2013 | Ohashi et al. |
| 8,598,070 | B1 | 12/2013 | Baugh et al. |
| 8,598,071 | B1 | 12/2013 | Baugh et al. |
| 8,809,561 | B2 | 8/2014 | Bellussi et al. |
| 9,181,282 | B2 | 11/2015 | Ide et al. |
| 2003/0188991 | A1 | 10/2003 | Shan et al. |
| 2005/0093189 | A1 | 5/2005 | Vo |
| 2006/0058565 | A1 | 3/2006 | DeWild |
| 2006/0070917 | A1 | 4/2006 | McCarthy et al. |
| 2006/0165574 | A1 | 7/2006 | Sayari |
| 2007/0034992 | A1 | 2/2007 | Wariishi et al. |
| 2007/0054136 | A1 | 3/2007 | Takahashi et al. |
| 2007/0112242 | A1 | 5/2007 | Edmiston |
| 2007/0173401 | A1 | 7/2007 | Landskron et al. |
| 2009/0130412 | A1 | 5/2009 | Hatton et al. |
| 2009/0215612 | A1 | 8/2009 | McCarthy et al. |
| 2009/0294922 | A1 | 12/2009 | Hamada et al. |
| 2010/0155302 | A1 | 6/2010 | Kaminsky et al. |
| 2010/0233482 | A1 | 9/2010 | Hamada et al. |
| 2011/0139685 | A1 | 6/2011 | McCarthy et al. |
| 2012/0059181 | A1 | 3/2012 | Bellussi et al. |
| 2012/0160742 | A1 | 6/2012 | Sohn et al. |
| 2013/0075876 | A1 | 3/2013 | Goethals et al. |
| 2013/0078172 | A1 | 3/2013 | Li et al. |
| 2013/0249049 | A1 | 9/2013 | Michalak et al. |
| 2014/0004358 | A1 | 1/2014 | Blackwell et al. |
| 2014/0186246 | A1 | 7/2014 | Calabro et al. |
| 2014/0208753 | A1 | 7/2014 | Liu et al. |
| 2015/0011787 | A1 | 1/2015 | Bellussi et al. |

FOREIGN PATENT DOCUMENTS

| | | |
|---|---|---|
| CN | 102052713 A | 5/2011 |
| CN | 102643429 A | 8/2012 |
| CN | 103157362 A | 6/2013 |
| CN | 103495340 A | 1/2014 |
| CN | 103613975 A | 3/2014 |
| CN | 104117343 A | 10/2014 |
| EP | 1995214 A2 | 11/2008 |
| JP | H10151343 A | 6/1998 |
| JP | H11295284 A | 10/1999 |

(56) References Cited

FOREIGN PATENT DOCUMENTS

| | | |
|---|---|---|
| JP | 2003167233 A | 6/2003 |
| JP | 2006083311 A | 3/2006 |
| JP | 2006095512 A | 4/2006 |
| JP | 2007070520 A | 3/2007 |
| JP | 2007238761 A | 9/2007 |
| JP | 2008045060 A | 2/2008 |
| JP | 2008062138 A | 3/2008 |
| JP | 2010100492 A | 5/2010 |
| JP | 2011025201 A | 2/2011 |
| JP | 2012149138 A | 8/2012 |
| JP | 2014057941 A | 4/2014 |
| JP | 5544672 B1 | 7/2014 |
| RU | 2291878 C1 | 1/2007 |
| WO | 9610537 A1 | 4/1996 |
| WO | 2006032140 A1 | 3/2006 |
| WO | 2007081212 A1 | 7/2007 |
| WO | 2011145933 A1 | 11/2011 |
| WO | 2013093022 A1 | 6/2013 |
| WO | 2014010512 A1 | 1/2014 |
| WO | 2014090757 A1 | 6/2014 |

OTHER PUBLICATIONS

Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.
Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.
Poli et al., "Different Routes for Preparing Mesoporous Organosilicas Containing the Troger's Base and Their Textural and Catalytic Implications", The Journal of Physical Chemistry C, Apr. 21, 2011, pp. 7573-7585, vol. 115, No. 15, ACS Publications.
PCT/US2015/065208 International Search Report and Written Opinion dated May 17, 2016.
PCT/US2015/065200 Partial International Search Report and Written Opinion dated May 23, 2016.
Diaz et al., "Hybrid organic-inorganic catalytic porous materials synthesized at neutral pH in absence of structural directing agents", Journal of Materials Chemistry, Jan. 1, 2009, pp. 5970-5979, vol. 19, No. 33, Royal Society of Chemistry.
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2016.
Topchiev et al., "Preparation of hexa alkoxy derivatives of cyclotrimethylenesilane", Doklady Akademii Nauk SSSR, 1955, pp. 95-96. vol. 103.
Kriner, "The preparation of cyclic siliconmethylene compounds", Journal of Organic Chemistry, Jun. 1964, pp. 1601-1606, vol. 29.
Kuivila et al., "Trimethylsilyl-substituted norbornenes, norbornanes, and nortricyclene", Journal of Organic Chemistry, Oct. 1964, pp. 2845-2851, vol. 29.
Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.

Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.
Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.
Melde et al., "Mesoporous Sieves with Unified Hybrid Inorganic/Organic Frameworks", Chemistry of Materials, Oct. 9, 1999, pp. 3302-3308, vol. 11.
Eliseeva et al., "Antifoaming additive for alkaline absorption solutions for removal of carbon dioxide from synthesis gas", Khimicheskaya Promyshlennost, 1999, pp. 632-633, vol. 10.
Brondani, et al., "Polyfunctional carbosilanes and organosilicon compounds. Synthesis via Grignard reactions", Tetrahedron Letters, Mar. 2, 2001, pp. 2111-2114, vol. 34.
Gilman et al., "Reactions of triphenylsilyllithium with some dichloropropenes", Journal of Organometallic Chemistry, Apr. 13, 2001, pp. 293-303, vol. 2.
Landskron et al., "Periodic Mesoporous Organosilicas Containing Interconnected [Si(CH2)]3 Rings", Science, Oct. 10, 2003, pp. 266-269, vol. 302.
Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.
Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.
Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.
Vidal et al., "Adsorption of polycyclic aromatic hydrocarbons from aqueous solutions by modified periodic mesoporous organosilica", Journal of Colloid and Interface Science, Feb. 3, 2011, pp. 466-473, vol. 357, No. 2.
Goethals et al., "Ultra-low-k cyclic carbon-bridged PMO films with a high chemical resistance", Journal of Materials Chemistry, Feb. 21, 2012, pp. 8281-8286, vol. 22.
PCT/US2015/065258 Partial International Search Report and Written Opinion dated Mar. 16, 2016.
PCT/US2015/065194 International Search Report and Written Opinion dated Mar. 29, 2016.
PCT/US2015/065191 International Search Report and Written Opinion dated Mar. 29, 2016.
PCT/US2015/065306 International Search Report and Written Opinion dated Mar. 29, 2016.
PCT/US2015/065219 International Search Report and Written Opinion dated Apr. 5, 2016.
PCT/US2015/065283 International Search Report and Written Opinion dated Apr. 6, 2016.
PCT/US2015/065199 International Search Report and Written Opinion dated Apr. 8, 2016.
PCT/US2015/065204 International Search Report and Written Opinion dated Apr. 8, 2016.
PCT/US2015/065225 International Search Report and Written Opinion dated Apr. 8, 2016.

AROMATIC HYDROGENATION CATALYSTS AND USES THEREOF

CROSS-REFERENCE TO RELATED APPLICATIONS

This application claims the benefit of provisional U.S. Ser. No. 62/091,071 and provisional U.S. Ser. No. 62/091,077, filed Dec. 12, 2014, the entire contents of which are expressly incorporated by reference herein.

This application is also related to several other U.S. applications, filed on even date herewith and bearing (entitled "Organosilica Materials and Uses Thereof"), 2014EM305-US2 (entitled "Methods of Producing Organosilica Materials and Uses Thereof"), 2015EM383 (entitled "Organosilica Materials and Uses Thereof"), 2015EM384 (entitled "Organosilica Materials and Uses Thereof"), 2015EM385 (entitled "Organosilica Materials and Uses Thereof"), 2015EM386 (entitled "Organosilica Materials and Uses Thereof"), 2015EM387 (entitled "Coating Method Using Organosilica Materials and Uses Thereof"), 2015EM388 (entitled "Membrane Fabrication Method Using Organosilica Materials and Uses Thereof"), 2015EM389 (entitled "Adsorbent for Heteroatom Species Removal and Uses Thereof"), and 2015EM390 (entitled "Method for Separating Aromatic Compounds from Lube Basestocks"), the entire disclosures of each of which are incorporated by reference herein.

Additionally, this application is further related to several other U.S. applications, filed on even date herewith and bearing (entitled "Organosilica Materials for Use as Adsorbents for Oxygenate Removal"), 2015EM376 (entitled "Supported Catalyst for Olefin Polymerization"), 2015EM377 (entitled "Supported Catalyst for Olefin Polymerization"), 2015EM378 (entitled "Supported Catalyst for Olefin Polymerization"), and 2015EM379 (entitled "Supported Catalyst for Olefin Polymerization"), the entire disclosures of each of which are incorporated by reference herein.

FIELD OF THE INVENTION

This invention relates to a catalyst and use of the catalyst for processing of hydrocarbon feedstreams that contain aromatics.

BACKGROUND OF THE INVENTION

Porous inorganic solids have found great utility as catalysts and separation media for industrial application. In particular, mesoporous materials, such as silicas and aluminas, having a periodic arrangement of mesopores are attractive materials for use in catalysis processes due to their uniform and tunable pores, high surface areas and large pore volumes. Such mesoporous materials are known to have large specific surface areas (e.g., 1000 m$^2$/g) and large pore volumes (e.g., 1 cm$^3$/g). For these reasons, such mesoporous materials enable reactive catalysts.

For example, hydrofinishing technologies have used both base and noble metal catalysts on a mesoporous support. With noble metal catalysts, excellent color and oxidation stability can be achieved at lower pressures and temperatures with smaller reactor volumes than those required when using base metal catalysts. At higher processing temperatures, color quality is sacrificed to achieve sufficient oxidation stability. With noble metal catalysts, it is possible to get superior color stability (water-white), excellent oxidation stability, and almost complete removal of aromatics.

However, mesoporous organosilicas, which may be used as a catalyst support, are conventionally formed by the self-assembly of the silsequioxane precursor in the presence of a structure directing agent, a porogen and/or a framework element. The precursor is hydrolysable and condenses around the structure directing agent. These materials have been referred to as Periodic Mesoporous Organosilicates (PMOs), due to the presence of periodic arrays of parallel aligned mesoscale channels. For example, Landskron, K., et al. [*Science*, 302:266-269 (2003)] report the self-assembly of 1,3,5-tris[diethoxysila]cylcohexane[(EtO)$_2$SiCH$_2$]$_3$ in the presence of a base and the structure directing agent, cetyl-trimethylammonium bromide, to form PMOs that are bridged organosilicas with a periodic mesoporous framework, which consist of SiO$_3$R or SiO$_2$R$_2$ building blocks, where R is a bridging organic group. In PMOs, the organic groups can be homogenously distributed in the pore walls. U.S. Pat. Pub. No. 2012/0059181 reports the preparation of a crystalline hybrid organic-inorganic silicate formed from 1,1,3,3,5,5 hexaethoxy-1,3,5 trisilyl cyclohexane in the presence of NaAlO$_2$ and base. U.S. Patent Application Publication No. 2007/003492 reports preparation of a composition formed from 1,1,3,3,5,5 hexaethoxy-1,3,5 trisilyl cyclohexane in the presence of propylene glycol monomethyl ether.

However, the use of a structure directing agent, such as a surfactant, in the preparation of an organosilica material, requires a complicated, energy intensive process to eliminate the structure directing agent at the end of the preparation process. For example, calcining may be required as well as wastewater disposal steps and associated costs to dispose of the structure directing agent. This limits the ability to scale-up the process for industrial applications.

Therefore, there is a need for improved catalysts and/or processes for aromatic saturation of hydrocarbon feeds using organosilica materials that can be prepared by a method that can be practiced in the absence of a structure directing agent, a porogen or surfactant.

SUMMARY OF THE INVENTION

It has been found that catalyst supports comprising organosilica material with desirable pore diameter, pore volume, and surface area can be achieved. Further, such organosilica material supports can be successfully prepared without the need for a structure directing agent, a porogen or surfactant.

Thus, in one aspect, embodiments of the invention provide a hydrogenation catalyst for aromatic hydrogenation comprising: (i) an organosilica material support, which is a polymer comprising independent units of a monomer of Formula [Z$^1$OZ$^2$OSiCH$_2$]$_3$ (I), wherein each Z$^1$ and Z$^2$ independently represent a hydrogen atom, a C$_1$-C$_4$ alkyl group or a bond to a silicon atom of another monomer; and (ii) at least one catalyst metal selected from the group consisting of a Group 8 metal, a Group 9 metal, a Group 10 metal and a combination thereof.

In still another aspect, embodiments of the invention provide a method of making a hydrogenation catalyst for aromatic hydrogenation, the method comprising: a) providing an aqueous mixture that contains essentially no structure directing agent and/or porogen, (b) adding at least one compound of Formula [Z$^{15}$Z$^{16}$SiCH$_2$]$_3$ (VII) into the aqueous mixture to form a solution, wherein each Z$^{15}$ represents a C$_1$-C$_4$ alkoxy group and each Z$^{16}$ represents a C$_1$-C$_4$ alkoxy group or a $C_1$-$C_4$ alkyl group; (c) aging the solution to produce a gel; (d) drying the gel to obtain an organosilica material support which is a polymer comprising independent units of a monomer of Formula $[Z^1OZ^2OSiCH_2]_3$ (I), wherein each $Z^1$ and $Z^2$ independently represent a hydrogen atom, a $C_1$-$C_4$ alkyl group or a bond to a silicon atom of another monomer; and (e) impregnating the organosilica material support with at least one catalyst metal selected from the group consisting of a Group 8 metal, a Group 9 metal, a Group 10 metal and a combination thereof.

In still another aspect, embodiments of the invention provide an aromatics hydrogenation process for a hydrocarbon feedstream comprising: a) contacting a hydrocarbon feedstream comprising aromatics with a hydrogenation catalyst in the presence of a hydrogen-containing treat gas in a first reaction stage operated under effective aromatics hydrogenation conditions to produce a reaction product with reduced aromatics content, wherein the hydrogenation catalyst comprises: (i) an organosilica material support, which is a polymer comprising independent units of a monomer of Formula $[Z^1OZ^2OSiCH_2]_3$ (I), wherein each $Z^1$ and $Z^2$ independently represent a hydrogen atom, a $C_1$-$C_4$ alkyl group or a bond to a silicon atom of another monomer; and (ii) at least one catalyst metal selected from the group consisting of a Group 8 metal, a Group 9 metal, a Group 10 metal and a combination thereof.

Other embodiments, including particular aspects of the embodiments summarized above, will be evident from the detailed description that follows.

DETAILED DESCRIPTION OF THE INVENTION

In various aspects of the invention, hydrogenation catalysts, methods for preparing hydrogenation catalysts and aromatics hydrogenation processes are provided.

I. Definitions

For purposes of this invention and the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i.e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and "$C_4$ alkyl" refers to butyl (e.g. —$CH_2CH_2CH_2CH_3$, —($CH_3$)$CHCH_2CH_3$, —$CH_2CH(CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

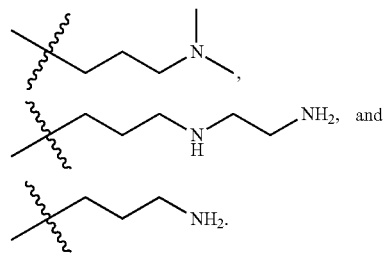

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

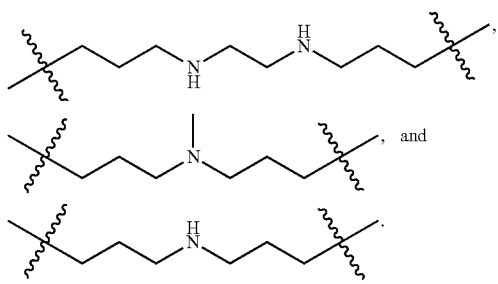

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —CH=CH—, —CH=CHCH$_2$—, —CH=CH=CH—, —CH$_2$CH$_2$CH=CHCH$_2$—, etc. —CH$_2$CH$_2$—, —CH(CH$_3$)CH$_2$—, —CH$_2$CH$_2$CH$_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompassses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —CH$_2$CH$_2$C≡CCH$_2$—, etc. —CH$_2$CH$_2$—, —CH(CH$_3$)CH$_2$—, —CH$_2$CH$_2$CH$_2$—, etc. The alkynlene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl).

Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group.

As used herein, the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

II. Hydrogenation Catalyst

The invention relates to hydrogenation catalysts, particularly for aromatic hydrogenation. In a first embodiment, a hydrogenation catalyst is provided comprising: (i) an organosilica material support, which is a polymer comprising independent units of a monomer of Formula $[Z^1OZ^2SiCH_2]_3$ (I), wherein each $Z^1$ and $Z^2$ independently can be a hydrogen atom, a $C_1$-$C_4$ alkyl group or a bond to a silicon atom of another monomer; and (ii) at least one catalyst metal selected from the group consisting of a Group 8 metal, a Group 9 metal, a Group 10 metal and a combination thereof.

As used herein, and unless otherwise specified, "a bond to a silicon atom of another monomer" means the bond can advantageously displace a moiety (particularly an oxygen-containing moiety such as a hydroxyl, an alkoxy or the like), if present, on a silicon atom of the another monomer so there may be a bond directly to the silicon atom of the another monomer thereby connecting the two monomers, e.g., via a Si—O—Si linkage. For clarity, in this bonding scenario, the "another monomer" can be a monomer of the same type or a monomer of a different type.

II.A. Organosilica Material Support

1. Monomers of Formula (I)

In various embodiments, the organosilica material support can be a polymer comprising independent units of a monomer of Formula $[Z^1OZ^2OSiCH_2]_3$ (I), wherein each $Z^1$ and/or $Z^2$ can be a hydrogen atom.

Additionally or alternatively, each $Z^1$ and/or $Z^2$ can be a $C_1$-$C_4$ alkyl group, a $C_1$-$C_3$ alkyl group, a $C_1$-$C_2$ alkyl group or methyl.

Additionally or alternatively, each $Z^1$ and/or $Z^2$ can be a bond to a silicon atom of another siloxane monomer.

Additionally or alternatively, each $Z^1$ and $Z^2$ independently can be a hydrogen atom, a $C_1$-$C_2$ alkyl group or a bond to a silicon atom of another monomer.

In a particular embodiment, each $Z^1$ and $Z^2$ independently can be a hydrogen atom, ethyl or a bond to a silicon atom of another monomer.

In another particular embodiment, each $Z^1$ and $Z^2$ independently can be a hydrogen atom or a bond to a silicon atom of another monomer.

2. Monomers of Formula (II)

In various embodiments, the organosilica material support may further comprise another monomer in combination with independent units of Formula (I), such as another monomer having at least one independent unit of Formula $[Z^3OZ^4SiCH_2]_3$ (II), wherein each $Z^3$ represents a hydrogen atom, a $C_1$-$C_4$ alkyl group or a bond to a silicon atom of another monomer and each $Z^4$ represents a $C_1$-$C_6$ alkyl group;

In various embodiments, each $Z^3$ can be a hydrogen atom.

Additionally or alternatively, each $Z^3$ can be a $C_1$-$C_4$ alkyl group, a $C_1$-$C_3$ alkyl group, a $C_1$-$C_2$ alkyl group or methyl.

Additionally or alternatively, each $Z^3$ can be a hydrogen atom or a $C_1$-$C_2$ alkyl group.

Additionally or alternatively, each $Z^3$ can be a bond to a silicon atom of another monomer.

Additionally or alternatively, each $Z^3$ can be a hydrogen atom, a $C_1$-$C_2$ alkyl group or a bond to a silicon atom of another monomer.

Additionally or alternatively, each $Z^3$ can be a hydrogen atom, ethyl or a bond to a silicon atom of another monomer.

Additionally or alternatively, each $Z^4$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^4$ can be a methyl.

Additionally or alternatively, each $Z^3$ can be a hydrogen atom, a $C_1$-$C_2$ alkyl group or a bond to a silicon atom of another monomer and each $Z^4$ can be a $C_1$-$C_4$ alkyl group.

Additionally or alternatively, each $Z^3$ can be a hydrogen atom, ethyl or a bond to a silicon atom of another monomer and each $Z^4$ can be methyl.

Additionally or alternatively, each $Z^3$ can be a hydrogen atom or a bond to a silicon atom of another monomer and each $Z^4$ can be methyl.

In another embodiment, the organosilica material support may comprise independent units of Formula $[Z^3OZ^4SiCH_2]_3$ (II) as described herein and not independent units of Formula (I) as described herein. In particular, each $Z^3$ can be a hydrogen atom, ethyl or a bond to a silicon atom of another monomer and each $Z^4$ can be methyl. Additionally or alternatively, each $Z^3$ can be a hydrogen atom or a bond to a silicon atom of another monomer and each $Z^4$ can be methyl.

3. Monomers of Formula (III)

In various embodiments, the organosilica material support may further comprise another monomer in combination with independent units of Formula (I) and optionally independent units of Formula (II), such as another monomer having at least one independent unit of Formula $Z^5OZ^6Z^7Z^8Si$ (III), wherein each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer.

As used herein, and unless otherwise specified, "an oxygen atom bonded to a silicon atom of another monomer" means that the oxygen atom can advantageously displace a moiety (particularly an oxygen-containing moiety such as a hydroxyl, an alkoxy or the like), if present, on a silicon atom of the another monomer so the oxygen atom may be bonded directly to the silicon atom of the another monomer thereby connecting the two monomers, e.g., via a Si—O—Si linkage. For clarity, in this bonding scenario, the "another monomer" can be a monomer of the same type or a monomer of a different type.

Additionally or alternatively, each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, and an oxygen atom bonded to a silicon atom of another monomer. Additionally or alternatively, $Z^6$, $Z^7$ and $Z^8$ each independently can optionally be a nitrogen-containing $C_1$-$C_{10}$ alkyl group, a nitrogen-containing heteroaralkyl group, and/or a nitrogen-containing optionally substituted heterocycloalkyl group.

In various aspects, each $Z^5$ can be a hydrogen atom.

Additionally or alternatively, each $Z^5$ can be a $C_1$-$C_4$ alkyl group, a $C_1$-$C_3$ alkyl group, a $C_1$-$C_2$ alkyl group or methyl.

Additionally or alternatively, each $Z^5$ can be a hydrogen atom or a $C_1$-$C_2$ alkyl group.

Additionally or alternatively, each $Z^5$ can be a bond to a silicon atom of another monomer.

Additionally or alternatively, each $Z^5$ can be a hydrogen atom, a $C_1$-$C_2$ alkyl group or a bond to a silicon atom of another monomer.

Additionally or alternatively, each $Z^5$ can be a hydrogen atom, ethyl, methyl or a bond to a silicon atom of another monomer.

Additionally or alternatively, $Z^6$, $Z^7$ and $Z^8$ each independently can be a hydroxyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group.

Additionally or alternatively, $Z^6$, $Z^7$ and $Z^8$ each independently can be a $C_1$-$C_4$ alkyl group, a $C_1$-$C_3$ alkyl group, a $C_1$-$C_2$ alkyl group or methyl.

Additionally or alternatively, $Z^6$, $Z^7$ and $Z^8$ each independently can be a hydroxyl group or a $C_1$-$C_2$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group or a $C_1$-$C_2$ alkyl group.

Additionally or alternatively, $Z^6$, $Z^7$ and $Z^8$ each independently can be a $C_1$-$C_4$ alkoxy group, a $C_1$-$C_3$ alkoxy group, a $C_1$-$C_2$ alkoxy group or methoxy.

Additionally or alternatively, $Z^6$, $Z^7$ and $Z^8$ each independently can be selected from the group consisting of a hydroxyl group, a $C_1$-$C_2$ alkyl group and a $C_1$-$C_2$ alkoxy group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each can be selected from the group consisting of a hydroxyl group, a $C_1$-$C_2$ alkyl group and a $C_1$-$C_2$ alkoxy group.

Additionally or alternatively, $Z^6$, $Z^7$ and $Z^8$ each independently can optionally be a nitrogen-containing $C_1$-$C_{10}$ alkyl group, a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^6$, $Z^7$ and $Z^8$ each independently can be a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

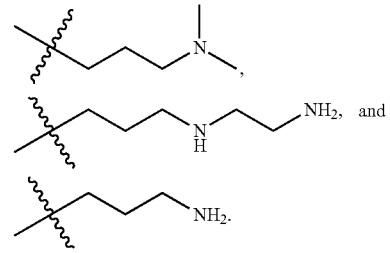

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, $Z^6$, $Z^7$ and $Z^8$ each independently can optionally be a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group and a nitrogen-containing heteroaralkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group and a nitrogen-containing heteroaralkyl group.

Additionally or alternatively, $Z^6$, $Z^7$ and $Z^8$ each independently can optionally be a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group, a nitrogen-containing heteroaralkyl group, and a nitrogen-containing optionally substituted heterocycloalkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group and a nitrogen-containing optionally substituted heterocycloalkyl group.

Additionally or alternatively, $Z^6$, $Z^7$ and $Z^8$ each independently optionally can be an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group, a nitrogen-containing optionally substituted heterocycloalkyl group and an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_8$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

Additionally or alternatively, each $Z^5$ can be a hydrogen atom or a bond to a silicon atom of another monomer; and $Z^6$, $Z^7$ and $Z^8$ each independently can be selected from the group consisting of a hydroxyl group, a $C_1$-$C_2$ alkyl group, a nitrogen-containing $C_3$-$C_8$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

In a particular embodiment, each $Z^5$ can be a hydrogen atom, ethyl or a bond to a silicon atom of another monomer; and $Z^6$, $Z^7$ and $Z^8$ each independently can be selected from the group consisting of a hydroxyl group, ethoxy, and an oxygen atom bonded to a silicon atom of another monomer.

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and $Z^8$ can be methyl.

In another particular embodiment, each $Z^5$ can be a hydrogen atom, methyl or a bond to a silicon atom of another comonomer; $Z^6$ and $Z^7$ each independently can be selected from the group consisting of a hydroxyl group, methoxy, and an oxygen atom bonded to a silicon atom of another monomer; and each $Z^8$ can be

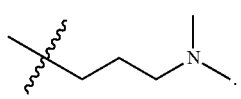 [SMILES: *CCCN(C)C]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

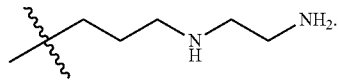 [SMILES: *CCCNCCN]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

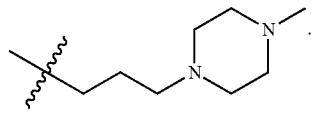 [SMILES: *CCCN1CCN(C)CC1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

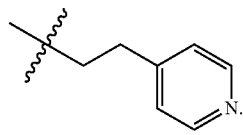 [SMILES: *CCc1ccncc1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

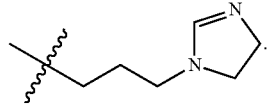 [SMILES: *CCCN1C=NCC1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

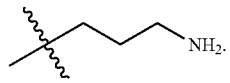 [SMILES: *CCCN]

In another embodiment, the organosilica material support may comprise independent units of Formula (II) as described herein and independent units of Formula (III) as described herein and not independent units of Formula (I) as described herein. In particular, each $Z^3$ can be a hydrogen atom, ethyl or a bond to a silicon atom of another monomer, each $Z^4$ can be methyl; each $Z^5$ can be a hydrogen atom, ethyl or a bond to a silicon atom of another monomer; and $Z^6$, $Z^7$ and $Z^8$ each independently can be selected from the group consisting of a hydroxyl group, ethoxy, and an oxygen atom bonded to a silicon atom of another monomer.

4. Monomers of Formula (IV)

In various embodiments, the organosilica material may further comprise another monomer in combination with independent units of Formula (I) and optionally independent units Formula (II) and/or Formula (III), such as another monomer having at least one independent unit of Formula $Z^9Z^{10}Z^{11}Si—R—SiZ^9Z^{10}Z^{11}$ (IV), wherein each $Z^9$ independently can be a hydroxyl group, a $C_1$-$C_4$ alkoxy group or an oxygen atom bonded to a silicon atom of another comonomer; each $Z^{10}$ and $Z^{11}$ independently can a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group.

Additionally or alternatively, each $Z^9$ independently can be a hydroxyl group, a $C_1$-$C_4$ alkoxy group or an oxygen atom bonded to a silicon atom of another comonomer; each $Z^{10}$ and $Z^{11}$ independently can a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, and a $C_2$-$C_8$ alkynylene group. Additionally or alternatively, R optionally can be a nitrogen-containing $C_1$-$C_{10}$ alkylene group, an optionally substituted $C_6$-$C_{20}$ aralkyl and/or an optionally substituted $C_4$-$C_{20}$ heterocycloalkyl group.

In various aspects, each $Z^9$ can be a hydroxyl group.

Additionally or alternatively, each $Z^9$ can be a $C_1$-$C_4$ alkoxy group, a $C_1$-$C_3$ alkoxy group, a $C_1$-$C_2$ alkoxy group or methoxy.

Additionally or alternatively, each $Z^9$ can be a hydroxyl group or a $C_1$-$C_2$ alkoxy group.

Additionally or alternatively, each $Z^9$ can be an oxygen atom bonded to a silicon atom of another comonomer.

Additionally or alternatively, each $Z^9$ can be a hydroxyl group, a $C_1$-$C_2$ alkoxy group or an oxygen atom bonded to a silicon atom of another comonomer.

Additionally or alternatively, each $Z^9$ can be a hydroxyl group or an oxygen atom bonded to a silicon atom of another comonomer.

Additionally or alternatively, each $Z^{10}$ and $Z^{11}$ independently can be a hydroxyl group.

Additionally or alternatively, each $Z^{10}$ and $Z^{11}$ independently can be a $C_1$-$C_4$ alkoxy group, a $C_1$-$C_3$ alkoxy group, a $C_1$-$C_2$ alkoxy group or methoxy.

Additionally or alternatively, each $Z^{10}$ and $Z^{11}$ independently can be a hydroxyl group or a $C_1$-$C_2$ alkoxy group.

Additionally or alternatively, each $Z^{10}$ and $Z^{11}$ independently can be a $C_1$-$C_4$ alkyl group, a $C_1$-$C_3$ alkyl group, a $C_1$-$C_2$ alkyl group or methyl.

Additionally or alternatively, each $Z^{10}$ and $Z^{11}$ independently can be a hydroxyl group, a $C_1$-$C_2$ alkoxy group, or a $C_1$-$C_2$ alkyl group.

Additionally or alternatively, each $Z^{10}$ and $Z^{11}$ independently can be an oxygen atom bonded to a silicon atom of another comonomer.

Additionally or alternatively, each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer.

Additionally or alternatively, each $Z^{10}$ and $Z^{11}$ independently can be a hydroxyl group, a $C_1$-$C_2$ alkyl group, or an oxygen atom bonded to a silicon atom of another comonomer.

Additionally or alternatively, each $Z^9$ can be a hydroxyl group, a $C_1$-$C_2$ alkoxy group or an oxygen atom bonded to a silicon atom of another comonomer; and each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer.

Additionally or alternatively, each $Z^9$ can be a hydroxyl group, ethoxy, methoxy or an oxygen atom bonded to a silicon atom of another comonomer; and each $Z^{10}$ and $Z^{11}$ independently can be a hydroxyl group, ethoxy, methyl, or an oxygen atom bonded to a silicon atom of another comonomer.

Additionally or alternatively, each $Z^9$ can be a hydroxyl group or an oxygen atom bonded to a silicon atom of another comonomer; and each $Z^{10}$ and $Z^{11}$ independently can be a hydroxyl group, methyl, or an oxygen atom bonded to a silicon atom of another comonomer.

Additionally or alternatively, each R can be a $C_1$-$C_8$ alkylene group, a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group or —$CH_2$—.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be a $C_1$-$C_4$ alkylene group.

Additionally or alternatively, each R can be a $C_2$-$C_8$ alkenylene group, a $C_2$-$C_7$ alkenylene group, a $C_2$-$C_6$ alkenylene group, a $C_2$-$C_5$ alkenylene group, a $C_2$-$C_4$ alkenylene group, a $C_2$-$C_3$ alkenylene group, or —HC=CH—.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group and a $C_2$-$C_4$ alkenylene group.

Additionally or alternatively, each R can be a $C_2$-$C_8$ alkynylene group, a $C_2$-$C_7$ alkynylene group, a $C_2$-$C_6$ alkynylene group, a $C_2$-$C_5$ alkynylene group, a $C_2$-$C_4$ alkynylene group, a $C_2$-$C_3$ alkynylene group, or —C≡C—.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group and a $C_2$-$C_4$ alkynylene group.

Additionally or alternatively, each R can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

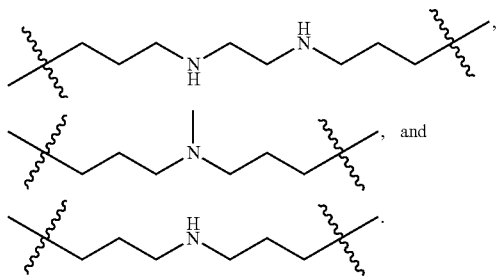

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group, a $C_2$-$C_4$ alkynylene group and a nitrogen-containing $C_4$-$C_{10}$ alkylene group.

Additionally or alternatively, each R can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenylmethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group and an optionally substituted $C_6$-$C_{10}$ aralkyl.

Additionally or alternatively, each R can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{10}$ heterocycloalkyl group.

Additionally or alternatively, each $Z^9$ can be a hydroxyl group, ethoxy, methoxy or an oxygen atom bonded to a silicon atom of another comonomer; each $Z^{10}$ and $Z^{11}$ independently can be a hydroxyl group, ethoxy, methoxy, methyl, or an oxygen atom bonded to a silicon atom of another comonomer; and R can be selected from the group consisting of —$CH_2$—, —$CH_2CH_2$—, —$HC$=$CH$—,

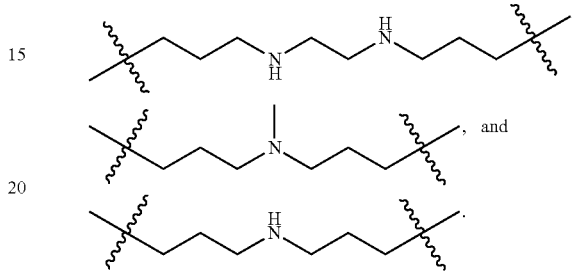

Additionally or alternatively, each $Z^9$ can be a hydroxyl group or an oxygen atom bonded to a silicon atom of another comonomer; each $Z^{10}$ and $Z^{11}$ independently can be a hydroxyl group, methyl, or an oxygen atom bonded to a silicon atom of another comonomer; and each R can be selected from the group consisting of —$CH_2$—,

—$CH_2CH_2$—, —$HC$=$CH$—,

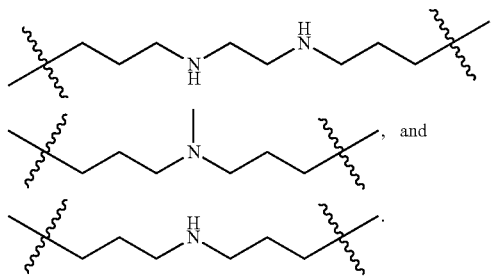

In a particular embodiment, each $Z^9$ can be a hydroxyl group, ethoxy or an oxygen atom bonded to a silicon atom of another comonomer; each $Z^{10}$ can be a hydroxyl group, ethoxy, and an oxygen atom bonded to a silicon atom of another monomer; each $Z^{11}$ can be methyl; and each R can be —$CH_2CH_2$—.

In another particular embodiment, each $Z^9$ can be a hydroxyl group, ethoxy or an oxygen atom bonded to a silicon atom of another comonomer; each $Z^{10}$ and $Z^{11}$ independently can be selected from the group consisting of a hydroxyl group, ethoxy, and an oxygen atom bonded to a silicon atom of another monomer; and R can be —$CH_2$—.

In another particular embodiment, each $Z^9$ can be a hydroxyl group, ethoxy or an oxygen atom bonded to a silicon atom of another comonomer; each $Z^{10}$ and $Z^{11}$ independently can be selected from the group consisting of a hydroxyl group, ethoxy, and an oxygen atom bonded to a silicon atom of another monomer; and R can be —$HC$=$CH$—.

In another particular embodiment, each $Z^9$ can be a hydroxyl group, methoxy or an oxygen atom bonded to a silicon atom of another comonomer; each $Z^{10}$ and $Z^{11}$ independently can be selected from the group consisting of a hydroxyl group, methoxy, and an oxygen atom bonded to a silicon atom of another monomer; and each R can be

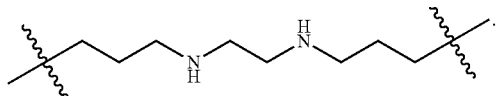 [SMILES: *CCCNCCNCCC*]

In another particular embodiment, each $Z^9$ can be a hydroxyl group, ethoxy or an oxygen atom bonded to a silicon atom of another comonomer; each $Z^{10}$ can be a hydroxyl group, ethoxy, and an oxygen atom bonded to a silicon atom of another monomer; each $Z''$ can be methyl; and each R can be

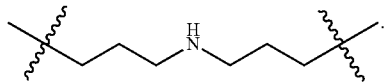 [SMILES: *CCCNCCC*]

In another particular embodiment, each $Z^9$ can be a hydroxyl group, methoxy or an oxygen atom bonded to a silicon atom of another comonomer; each $Z^{10}$ can be a hydroxyl group, methoxy, and an oxygen atom bonded to a silicon atom of another monomer; each $Z^{11}$ can be methyl; and each R can be

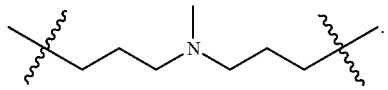 [SMILES: *CCCN(C)CCC*]

In another embodiment, the organosilica material support may comprise independent units of Formula (III) as described herein and independent units of Formula (IV) as described herein and not independent units of Formula (I) as described herein. In particular, each $Z^5$ can be a hydrogen atom, ethyl or a bond to a silicon atom of another monomer; $Z^6$, $Z^7$ and $Z^8$ each independently can be selected from the group consisting of a hydroxyl group, ethoxy, and an oxygen atom bonded to a silicon atom of another monomer and each $Z^9$ can be a hydroxyl group, ethoxy or an oxygen atom bonded to a silicon atom of another comonomer; each $Z^{10}$ and $Z^{11}$ independently can be selected from the group consisting of a hydroxyl group, ethoxy, and an oxygen atom bonded to a silicon atom of another monomer; and R can be —$CH_2$—.

5. Monomers of Formula (V)

In various embodiments, the organosilica material may further comprise another monomer in combination with independent units of Formula (I) and optionally independent units Formula (II), (III), (IV) and/or Formula (V), such as another monomer having at least one independent unit of Formula $M^1(OZ^{12})_3$ (V), wherein $M^1$ represents a Group 13 metal and each $Z^{12}$ independently represents a hydrogen atom, a $C_1$-$C_6$ alkyl or a bond to a silicon atom of another monomer;

Additionally or alternatively, $M^1$ can be B, Al, Ga, IN Tl, or Uut. In particular, $M^1$ can be Al or B.

Additionally or alternatively, each $Z^{12}$ can be a hydrogen atom.

Additionally or alternatively, $M^1$ can be Al or B and $Z^3$ can be a hydrogen atom.

Additionally or alternatively, each $Z^{12}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^3$ can be methyl, ethyl, propyl or butyl.

Additionally or alternatively, $M^1$ can be Al or B and $Z^{12}$ can be a hydrogen atom, methyl, ethyl, propyl or butyl.

Additionally or alternatively, each $Z^{12}$ can be a bond to a silicon atom of another monomer.

Additionally or alternatively, $M^1$ can be Al or B and each $Z^{12}$ can be a hydrogen atom, methyl, ethyl, propyl, butyl or a bond to a silicon atom of another monomer.

Additionally or alternatively, $M^1$ can be Al or B and each $Z^{12}$ can be a hydrogen atom or a bond to a silicon atom of another monomer.

Additionally or alternatively, $M^1$ can be Al and each $Z^{12}$ can be a hydrogen atom, methyl, ethyl, propyl, butyl or a bond to a silicon atom of another monomer.

In a particular embodiment, $M^1$ can be Al and each $Z^{12}$ can be a hydrogen atom, methyl or a bond to a silicon atom of another monomer.

In another particular embodiment, $M^1$ can be Al and each $Z^{12}$ can be a hydrogen atom, ethyl or a bond to a silicon atom of another monomer.

In another particular embodiment, $M^1$ can be Al and each $Z^{12}$ can be a hydrogen atom, propyl or a bond to a silicon atom of another monomer.

In another particular embodiment, $M^1$ can be Al and each $Z^{12}$ can be a hydrogen atom, butyl or a bond to a silicon atom of another monomer.

In another particular embodiment, $M^1$ can be Al or B; and each $Z^{12}$ can be a hydrogen atom or a bond to a silicon atom of another monomer.

6. Monomers of Formula (VI)

In various embodiments, the organosilica material may further comprise another monomer in combination with independent units of Formula (I) and optionally independent units Formula (II), (III) and/or Formula (IV), such as another monomer having at least one independent unit of Formula $(Z^{13}O)_2M^2$-O-$Si(OZ^{14})_3$ (VI), wherein $M^2$ represents a Group 13 metal and each $Z^{13}$ and each $Z^{14}$ independently represent a hydrogen atom, a $C_1$-$C_6$ alkyl group or a bond to a silicon atom of another monomer.

Additionally or alternatively, $M^2$ can be B, Al, Ga, IN Tl, or Uut. In particular, $M^2$ can be Al or B.

Additionally or alternatively, each $Z^{13}$ and/or $Z^{14}$ can be a hydrogen atom.

Additionally or alternatively, $M^2$ can be Al or B and each $Z^{13}$ and/or each $Z^{14}$ can be a hydrogen atom.

Additionally or alternatively, $Z^{13}$ and/or $Z^{14}$ each can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{13}$ and/or $Z^{14}$ can be methyl, ethyl, propyl or butyl.

Additionally or alternatively, $M^2$ can be Al or B; and $Z^{13}$ and/or $Z^{14}$ independently can be a hydrogen atom, methyl, ethyl, propyl or butyl.

Additionally or alternatively, each $Z^{13}$ and/or each $Z^{14}$ each can be a bond to a silicon atom of another monomer.

Additionally or alternatively, $M^2$ can be Al or B; and each $Z^{13}$ and each $Z^{14}$ independently can be a hydrogen atom, methyl, ethyl, propyl, butyl or a bond to a silicon atom of another monomer.

Additionally or alternatively, $M^2$ can be Al or B; and each $Z^{13}$ and each $Z^{14}$ independently can be a hydrogen atom or a bond to a silicon atom of another monomer.

Additionally or alternatively, $M^2$ can be Al; and each $Z^{13}$ and each $Z^{14}$ independently can be a hydrogen atom, methyl, ethyl, propyl, butyl or a bond to a silicon atom of another monomer.

In a particular embodiment, $M^2$ can be Al; and each $Z^{13}$ and each $Z^{14}$ independently can be a hydrogen atom, methyl or a bond to a silicon atom of another monomer.

In another particular embodiment, $M^2$ can be Al; and each $Z^{13}$ and each $Z^{14}$ independently can be a hydrogen atom, ethyl or a bond to a silicon atom of another monomer.

In another particular embodiment, $M^2$ can be Al; and each $Z^{13}$ and each $Z^{14}$ independently can be a hydrogen atom, propyl or a bond to a silicon atom of another monomer.

In another particular embodiment, $M^2$ can be Al; and each $Z^{13}$ and each $Z^{14}$ independently can be a hydrogen atom, butyl or a bond to a silicon atom of another monomer.

In another particular embodiment, $M^2$ can be Al or B; and each $Z^{13}$ and each $Z^{14}$ independently can be a hydrogen atom or a bond to a silicon atom of another monomer.

The organosilica material supports described herein can be characterized as described in the following sections.

7. X-Ray Diffraction Peaks

The organosilica material supports described herein can exhibit powder X-ray diffraction patterns with one broad peak between about 1 and about 4 degrees 2θ, particularly one broad peak between about 1 and about 3 degrees 2θ. Additionally or alternatively, the organosilica materials can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

8. Silanol Content

The organosilica material supports described can have a silanol content that varies within wide limits, depending on the composition of the synthesis solution. The silanol content can conveniently be determined by solid state silicon NMR.

In various aspects, the organosilica material supports can have a silanol content of greater than about 5%, greater than about 10%, greater than about 15%, greater than about 20%, greater than about 25%, greater than about 30%, greater than about 33%, greater than 35%, greater than about 40%, greater than about 41%, greater than about 44%, greater than about 45%, greater than about 50%, greater than about 55%, greater than about 60%, greater than about 65%, greater than about 70%, greater than about 75%, or about 80%. In certain embodiments, the silanol content can be greater than about 30% or greater than about 41%.

Additionally or alternatively, the organosilica material supports may have a silanol content of about 5% to about 80%, about 5% to about 75%, about 5% to about 70%, about 5% to about 65%, about 5% to about 60%, about 5% to about 55%, about 5% to about 50%, about 5% to about 45%, about 5% to about 44%, about 5% to to about 41%, about 5% to about 40%, about 5% to about 35%, about 5% to about 33%, about 5% to about 30%, about 5% to about 25%, about 5% to about 20%, about 5% to about 15%, about 5% to about 10%, about 10% to about 80%, about 10% to about 75%, about 10% to about 70%, about 10% to about 65%, about 10% to about 60%, about 10% to about 55%, about 10% to about 50%, about 10% to about 45%, about 10% to about 44%, about 10% to about 41%, about 10% to about 40%, about 10% to about 35%, about 10% to about 33%, about 10% to about 30%, about 10% to about 25%, about 10% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 44%, about 20% to about 41%, about 20% to about 40%, about 20% to about 35%, about 20% to about 33%, about 20% to about 30%, about 20% to about 25%, about 30% to about 80%, about 30% to about 75%, about 30% to about 70%, about 30% to about 65%, about 30% to about 60%, about 30% to about 55%, about 30% to about 50%, about 30% to about 45%, about 30% to about 44%, about 30% to about 41%, about 30% to about 40%, about 30% to about 35%, about 30% to about 33%, about 40% to about 80%, about 40% to about 75%, about 40% to about 70%, about 40% to about 65%, about 40% to about 60%, about 40% to about 55%, about 40% to about 50%, about 40% to about 45%, about 40% to about 44%, or about 40% to about 41%.

9. Pore Size

The organosilica material supports described herein are advantageously in a mesoporous form. As indicated previously, the term mesoporous refers to solid materials having pores with a diameter within the range of from about 2 nm to about 50 nm. The average pore diameter of the organosilica material can be determined, for example, using nitrogen adsorption-desorption isotherm techniques within the expertise of one of skill in the art, such as the BET (Brunauer Emmet Teller) method.

The organosilica material supports can have an average pore diameter of about 0.2 nm, about 0.4 nm, about 0.5 nm, about 0.6 nm, about 0.8 nm, about 1.0 nm, about 1.5 nm, about 1.8 nm or less than about 2.0 nm.

Additionally or alternatively, the organosilica material supports can advantageously have an average pore diameter within the mesopore range of about 2.0 nm, about 2.5 nm, about 3.0 nm, about 3.1 nm, about 3.2 nm, about 3.3 nm, about 3.4 nm, about 3.5 nm, about 3.6 nm, about 3.7 nm, about 3.8 nm, about 3.9 nm about 4.0 nm, about 4.1 nm, about 4.5 nm, about 5.0 nm, about 6.0 nm, about 7.0 nm, about 7.3 nm, about 8 nm, about 8.4 nm, about 9 nm, about 10 nm, about 11 nm, about 13 nm, about 15 nm, about 18 nm, about 20 nm, about 23 nm, about 25 nm, about 30 nm, about 40 nm, about 45 nm, or about 50 nm.

Additionally or alternatively, the organosilica material supports can have an average pore diameter of 0.2 nm to about 50 nm, about 0.2 nm to about 40 nm, about 0.2 nm to about 30 nm, about 0.2 nm to about 25 nm, about 0.2 nm to about 23 nm, about 0.2 nm to about 20 nm, about 0.2 nm to about 18 nm, about 0.2 nm to about 15 nm, about 0.2 nm to about 13 nm, about 0.2 nm to about 11 nm, about 0.2 nm to about 10 nm, about 0.2 nm to about 9 nm, about 0.2 nm to about 8.4 nm, about 0.2 nm to about 8 nm, about 0.2 nm to about 7.3 nm, about 0.2 nm to about 7.0 nm, about 0.2 nm to about 6.0 nm, about 0.2 nm to about 5.0 nm, about 0.2 nm to about 4.5 nm, about 0.2 nm to about 4.1 nm, about 0.2 nm to about 4.0 nm, about 0.2 nm to about 3.9 nm, about 0.2 nm to about 3.8 nm, about 0.2 nm to about 3.7 nm, about 0.2 nm to about 3.6 nm, about 0.2 nm to about 3.5 nm, about 0.2 nm to about 3.4 nm, about 0.2 nm to about 3.3 nm, about 0.2 nm to about 3.2 nm, about 0.2 nm to about 3.1 nm, about 0.2 nm to about 3.0 nm, about 0.2 nm to about 2.5 nm, about 0.2 nm to about 2.0 nm, about 0.2 nm to about 1.0 nm, about 1.0 nm to about 50 nm, about 1.0 nm to about 40 nm, about 1.0 nm to about 30 nm, about 1.0 nm to about 25 nm, about 1.0 nm to about 23 nm, about 1.0 nm to about 20 nm, about 1.0 nm to about 18 nm, about 1.0 nm to about 15 nm, about 1.0 nm to about 13 nm, about 1.0 nm to about 11 nm, about 1.0 nm to about 10 nm, about 1.0 nm to about 9 nm, about 1.0 nm to about 8.4 nm, about 1.0 nm to about 8 nm, about 1.0 nm to about 7.3 nm, about 1.0 nm to about 7.0 nm, about 1.0 nm to about 6.0 nm, about 1.0 nm to about 5.0 nm, about 1.0 nm to about 4.5 nm, about 1.0 nm to about 4.1 nm, about 1.0 nm to about 4.0 nm, about 1.0 nm to about 3.9 nm, about 1.0 nm to about 3.8 nm, about 1.0 nm to about 3.7 nm, about 1.0 nm to about 3.6 nm, about 1.0 nm to about 3.5 nm, about 1.0 nm to about 3.4 nm, about 1.0 nm to about 3.3 nm, about 1.0 nm to about 3.2 nm, about 1.0 nm to about 3.1 nm, about 1.0 nm to about 3.0 nm or about 1.0 nm to about 2.5 nm.

In particular, the organosilica material supports can advantageously have an average pore diameter in the mesopore range of about 2.0 nm to about 50 nm, about 2.0 nm to about 40 nm, about 2.0 nm to about 30 nm, about 2.0 nm to about 25 nm, about 2.0 nm to about 23 nm, about 2.0 nm to about 20 nm, about 2.0 nm to about 18 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.4 nm, about 2.0 nm to about 8 nm, about 2.0 nm to about 7.3 nm, about 2.0 nm to about 7.0 nm, about 2.0 nm to about 6.0 nm, about 2.0 nm to about 5.0 nm, about 2.0 nm to about 4.5 nm, about 2.0 nm to about 4.1 nm, about 2.0 nm to about 4.0 nm, about 2.0 nm to about 3.9 nm, about 2.0 nm to about 3.8 nm, about 2.0 nm to about 3.7 nm, about 2.0 nm to about 3.6 nm, about 2.0 nm to about 3.5 nm, about 2.0 nm to about 3.4 nm, about 2.0 nm to about 3.3 nm, about 2.0 nm to about 3.2 nm, about 2.0 nm to about 3.1 nm, about 2.0 nm to about 3.0 nm, about 2.0 nm to about 2.5 nm, about 2.5 nm to about 50 nm, about 2.5 nm to about 40 nm, about 2.5 nm to about 30 nm, about 2.5 nm to about 25 nm, about 2.5 nm to about 23 nm, about 2.5 nm to about 20 nm, about 2.5 nm to about 18 nm, about 2.5 nm to about 15 nm, about 2.5 nm to about 13 nm, about 2.5 nm to about 11 nm, about 2.5 nm to about 10 nm, about 2.5 nm to about 9 nm, about 2.5 nm to about 8.4 nm, about 2.5 nm to about 8 nm, about 2.5 nm to about 7.3 nm, about 2.5 nm to about 7.0 nm, about 2.5 nm to about 6.0 nm, about 2.5 nm to about 5.0 nm, about 2.5 nm to about 4.5 nm, about 2.5 nm to about 4.1 nm, about 2.5 nm to about 4.0 nm, about 2.5 nm to about 3.9 nm, about 2.5 nm to about 3.8 nm, about 2.5 nm to about 3.7 nm, about 2.5 nm to about 3.6 nm, about 2.5 nm to about 3.5 nm, about 2.5 nm to about 3.4 nm, about 2.5 nm to about 3.3 nm, about 2.5 nm to about 3.2 nm, about 2.5 nm to about 3.1 nm, about 2.5 nm to about 3.0 nm, about 3.0 nm to about 50 nm, about 3.0 nm to about 40 nm, about 3.0 nm to about 30 nm, about 3.0 nm to about 25 nm, about 3.0 nm to about 23 nm, about 3.0 nm to about 20 nm, about 3.0 nm to about 18 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.4 nm, about 3.0 nm to about 8 nm, about 3.0 nm to about 7.3 nm, about 3.0 nm to about 7.0 nm, about 3.0 nm to about 6.0 nm, about 3.0 nm to about 5.0 nm, about 3.0 nm to about 4.5 nm, about 3.0 nm to about 4.1 nm, or about 3.0 nm to about 4.0 nm.

In one particular embodiment, the organosilica material supports described herein can have an average pore diameter of about 1.0 nm to about 30.0 nm, particularly about 1.0 nm to about 25.0 nm, particularly about 2.0 nm to about 25.0 nm, particularly about 2.0 nm to about 20.0 nm, particularly about 2.0 nm to about 15.0 nm, particularly about 2.0 nm to about 10.0 nm, or particularly about 3.0 nm to about 10.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from $N_2$ adsorption isotherm experiments. In such circumstances, without being bound by theory, the hysteresis can result from the lack of regularity in the pore shapes/sizes and/or from bottleneck constrictions in such irregular pores.

10. Surface Area

The surface area of the organosilica material supports can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method.

In various embodiments, the organosilica material supports can have a total surface area greater than or equal to about 100 $m^2/g$, greater than or equal to about 200 $m^2/g$, greater than or equal to about 300 $m^2/g$, greater than or equal to about 400 $m^2/g$, greater than or equal to about 450 $m^2/g$, greater than or equal to about 500 $m^2/g$, greater than or equal to about 550 $m^2/g$, greater than or equal to about 600 $m^2/g$, greater than or equal to about 700 $m^2/g$, greater than or equal to about 800 $m^2/g$, greater than or equal to about 850 $m^2/g$, greater than or equal to about 900 $m^2/g$, greater than or equal to about 1,000 $m^2/g$, greater than or equal to about 1,050 $m^2/g$, greater than or equal to about 1,100 $m^2/g$, greater than or equal to about 1,150 $m^2/g$, greater than or equal to about 1,200 $m^2/g$, greater than or equal to about 1,250 $m^2/g$, greater than or equal to about 1,300 $m^2/g$, greater than or equal to about 1,400 $m^2/g$, greater than or equal to about 1,450 $m^2/g$, greater than or equal to about 1,500 $m^2/g$, greater than or equal to about 1,550 $m^2/g$, greater than or equal to about 1,600 $m^2/g$, greater than or equal to about 1,700 $m^2/g$, greater than or equal to about 1,800 $m^2/g$, greater than or equal to about 1,900 $m^2/g$, greater than or equal to about 2,000 $m^2/g$, greater than or equal to greater than or equal to about 2,100 $m^2/g$, greater than or equal to about 2,200 $m^2/g$, greater than or equal to about 2,300 $m^2/g$ or about 2,500 $m^2/g$.

Additionally or alternatively, the organosilica material supports may have a total surface area of about 50 $m^2/g$ to about 2,500 $m^2/g$, about 50 $m^2/g$ to about 2,000 $m^2/g$, about 50 $m^2/g$ to about 1,500 $m^2/g$, about 50 $m^2/g$ to about 1,000 $m^2/g$, about 100 $m^2/g$ to about 2,500 $m^2/g$, about 100 $m^2/g$ to about 2,300 $m^2/g$, about 100 $m^2/g$ to about 2,200 $m^2/g$, about 100 $m^2/g$ to about 2,100 $m^2/g$, about 100 $m^2/g$ to about 2,000 $m^2/g$, about 100 $m^2/g$ to about 1,900 $m^2/g$, about 100 $m^2/g$ to about 1,800 $m^2/g$, about 100 $m^2/g$ to about 1,700 $m^2/g$, about 100 $m^2/g$ to about 1,600 $m^2/g$, about 100 $m^2/g$ to about 1,550 $m^2/g$, about 100 $m^2/g$ to about 1,500 $m^2/g$, about 100 $m^2/g$ to about 1,450 $m^2/g$, about 100 $m^2/g$ to about 1,400 $m^2/g$, about 100 $m^2/g$ to about 1,300 $m^2/g$, about 100 m²/g to about 1,250 m²/g, about 100 m²/g to about 1,200 m²/g, about 100 m²/g to about 1,150 m²/g, about 100 m²/g to about 1,100 m²/g, about 100 m²/g to about 1,050 m²/g, about 100 m²/g to about 1,000 m²/g, about 100 m²/g to about 900 m²/g, about 100 m²/g to about 850 m²/g, about 100 m²/g to about 800 m²/g, about 100 m²/g to about 700 m²/g, about 100 m²/g to about 600 m²/g, about 100 m²/g to about 550 m²/g, about 100 m²/g to about 500 m²/g, about 100 m²/g to about 450 m²/g, about 100 m²/g to about 400 m²/g, about 100 m²/g to about 300 m²/g, about 100 m²/g to about 200 m²/g, about 200 m²/g to about 2,500 m²/g, about 200 m²/g to about 2,300 m²/g, about 200 m²/g to about 2,200 m²/g, about 200 m²/g to about 2,100 m²/g, about 200 m²/g to about 2,000 m²/g, about 200 m²/g to about 1,900 m²/g, about 200 m²/g to about 1,800 m²/g, about 200 m²/g to about 1,700 m²/g, about 200 m²/g to about 1,600 m²/g, about 200 m²/g to about 1,550 m²/g, about 200 m²/g to about 1,500 m²/g, about 200 m²/g to about 1,450 m²/g, about 200 m²/g to about 1,400 m²/g, about 200 m²/g to about 1,300 m²/g, about 200 m²/g to about 1,250 m²/g, about 200 m²/g to about 1,200 m²/g, about 200 m²/g to about 1,150 m²/g, about 200 m²/g to about 1,100 m²/g, about 200 m²/g to about 1,050 m²/g, about 200 m²/g to about 1,000 m²/g, about 200 m²/g to about 900 m²/g, about 200 m²/g to about 850 m²/g, about 200 m²/g to about 800 m²/g, about 200 m²/g to about 700 m²/g, about 200 m²/g to about 600 m²/g, about 200 m²/g to about 550 m²/g, about 200 m²/g to about 500 m²/g, about 200 m²/g to about 450 m²/g, about 200 m²/g to about 400 m²/g, about 200 m²/g to about 300 m²/g, about 500 m²/g to about 2,500 m²/g, about 500 m²/g to about 2,300 m²/g, about 500 m²/g to about 2,200 m²/g, about 500 m²/g to about 2,100 m²/g, about 500 m²/g to about 2,000 m²/g, about 500 m²/g to about 1,900 m²/g, about 500 m²/g to about 1,800 m²/g, about 500 m²/g to about 1,700 m²/g, about 500 m²/g to about 1,600 m²/g, about 500 m²/g to about 1,550 m²/g, about 500 m²/g to about 1,500 m²/g, about 500 m²/g to about 1,450 m²/g, about 500 m²/g to about 1,400 m²/g, about 500 m²/g to about, 300 m²/g, about 500 m²/g to about 1,250 m²/g, about 500 m²/g to about 1,200 m²/g, about 500 m²/g to about 1,150 m²/g, about 500 m²/g to about 1,100 m²/g, about 500 m²/g to about 1,050 m²/g, about 500 m²/g to about 1,000 m²/g, about 500 m²/g to about 900 m²/g, about 500 m²/g to about 850 m²/g, about 500 m²/g to about 800 m²/g, about 500 m²/g to about 700 m²/g, about 500 m²/g to about 600 m²/g, about 500 m²/g to about 550 m²/g, about 1,000 m²/g to about 2,500 m²/g, about 1,000 m²/g to about 2,300 m²/g, about 1,000 m²/g to about 2,200 m²/g, about 1,000 m²/g to about 2,100 m²/g, about 1,000 m²/g to about 2,000 m²/g, about 1,000 m²/g to about 1,900 m²/g, about 1,000 m²/g to about 1,800 m²/g, about 1,000 m²/g to about 1,700 m²/g, about 1,000 m²/g to about 1,600 m²/g, about 1,000 m²/g to about 1,550 m²/g, about 1,000 m²/g to about 1,500 m²/g, about 1,000 m²/g to about 1,450 m²/g, about 1,000 m²/g to about 1,400 m²/g, about 1,000 m²/g to about 1,300 m²/g, about 1,000 m²/g to about 1,250 m²/g, about 1,000 m²/g to about 1,200 m²/g, about 1,000 m²/g to about 1,150 m²/g, about 1,000 m²/g to about 1,100 m²/g, or about 1,000 m²/g to about 1,050 m²/g.

In one particular embodiment, the organosilica material supports described herein may have a total surface area of about 200 m²/g to about 2,500 m²/g, particularly about 400 m²/g to about 2,500 m²/g, particularly about 400 m²/g to about 2,000 m²/g, particularly about 500 m²/g to about 2,000 m²/g, or particularly about 400 m²/g to about 1,500 m²/g.

11. Pore Volume

The pore volume of the organosilica material supports made by the methods described herein can be determined, for example, using nitrogen adsorption-desorption isotherm techniques within the expertise of one of skill in the art, such as the BET (Brunauer Emmet Teller) method.

In various embodiments, the organosilica material can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, greater than or equal to about 1.5 cm³/g, greater than or equal to about 1.6 cm³/g, greater than or equal to about 1.7 cm³/g, greater than or equal to about 1.8 cm³/g, greater than or equal to about 1.9 cm³/g, greater than or equal to about 2.0 cm³/g, greater than or equal to about 2.5 cm³/g, greater than or equal to about 3.0 cm³/g, greater than or equal to about 3.5 cm³/g, greater than or equal to about 4.0 cm³/g, greater than or equal to about 5.0 cm³/g, greater than or equal to about 6.0 cm³/g, greater than or equal to about 7.0 cm³/g, or about 10.0 cm³/g.

Additionally or alternatively, the organosilica material supports can have a pore volume of about 0.1 cm³/g to about 10.0 cm³/g, about 0.1 cm³/g to about 7.0 cm³/g, about 0.1 cm³/g to about 6.0 cm³/g, about 0.1 cm³/g to about 5.0 cm³/g, about 0.1 cm³/g to about 4.0 cm³/g, about 0.1 cm³/g to about 3.5 cm³/g, about 0.1 cm³/g to about 3.0 cm³/g, about 0.1 cm³/g to about 2.5 cm³/g, about 0.1 cm³/g to about 2.0 cm³/g, about 0.1 cm³/g to about 1.9 cm³/g, about 0.1 cm³/g to about 1.8 cm³/g, about 0.1 cm³/g to about 1.7 cm³/g, about 0.1 cm³/g to about 1.6 cm³/g, about 0.1 cm³/g to about 1.5 cm³/g, about 0.1 cm³/g to about 1.4 cm³/g, about 0.1 cm³/g to about 1.3 cm³/g, about 0.1 cm³/g to about 1.2 cm³/g, about 0.1 cm³/g to about 1.1, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.1 cm³/g to about 0.2 cm³/g, 0.2 cm³/g to about 10.0 cm³/g, about 0.2 cm³/g to about 7.0 cm³/g, about 0.2 cm³/g to about 6.0 cm³/g, about 0.2 cm³/g to about 5.0 cm³/g, about 0.2 cm³/g to about 4.0 cm³/g, about 0.2 cm³/g to about 3.5 cm³/g, about 0.2 cm³/g to about 3.0 cm³/g, about 0.2 cm³/g to about 2.5 cm³/g, about 0.2 cm³/g to about 2.0 cm³/g, about 0.2 cm³/g to about 1.9 cm³/g, about 0.2 cm³/g to about 1.8 cm³/g, about 0.2 cm³/g to about 1.7 cm³/g, about 0.2 cm³/g to about 1.6 cm³/g, about 0.2 cm³/g to about 1.5 cm³/g, about 0.2 cm³/g to about 1.4 cm³/g, about 0.2 cm³/g to about 1.3 cm³/g, about 0.2 cm³/g to about 1.2 cm³/g, about 0.2 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, about 0.5 cm³/g to about 0.6 cm³/g, about 0.5 cm³/g to about 0.5 cm³/g, about 0.5 cm³/g to about 0.4 cm³/g, about 0.5 cm³/g to about 0.3 cm³/g, 0.5 cm³/g to about 10.0 cm³/g, about 0.5 cm³/g to about 7.0 cm³/g, about 0.5 cm³/g to about 6.0 cm³/g, about 0.5 cm³/g to about 5.0 cm³/g, about 0.5 cm³/g to about 4.0 cm³/g, about 0.5 cm³/g to about 3.5 cm³/g, about 0.5 cm³/g to about 3.0 cm³/g, about 0.5 cm³/g to about 2.5 cm³/g, about 0.5 cm³/g to about 2.0 cm³/g, about 0.5 cm³/g to about 1.9 cm³/g, about 0.5 cm³/g to about 1.8 cm³/g, about 0.5 cm³/g to about 1.7 cm³/g, about 0.5 cm³/g to about 1.6 cm³/g, about 0.5 cm³/g to about 1.5 cm³/g, about 0.5 cm³/g to about 1.4 cm³/g, about 0.5 cm³/g to about 1.3 cm³/g, about 0.5 cm³/g to about 1.2 cm³/g, about 0.5 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, or about 0.5 cm³/g to about 0.6 cm³/g.

In a particular embodiment, the organosilica material supports can have a pore volume of about 0.1 cm³/g to about 5.0 cm³/g, particularly about 0.1 cm³/g to about 3.0 cm³/g, particularly about 0.2 cm³/g to about 3.0 cm³/g, particularly about 0.2 cm³/g to about 2.5 cm³/g, or particularly about 0.2 cm³/g to about 1.5 cm³/g.

II.B. Catalyst Metal

The hydrogenation catalyst may further comprise at least one catalyst metal. The at least one catalyst metal may be incorporated within the pores of the organosilica material support. Exemplary catalyst metals can include, but are not limited to, a Group 6 metal, a Group 8 metal, a Group 9 metal, a Group 10 metal or a combination thereof. Exemplary Group 6 metals can include, but are not limited to, chromium, molybdenum, and/or tungsten, particularly including molybdenum and/or tungsten. Exemplary Group 8 metals can include, but are not limited to, iron, ruthenium, and/or osmium. Exemplary Group 9 metals can include, but are not limited to, cobalt, rhodium, and/or iridium, particularly including cobalt. Exemplary Group 10 metals can include, but are not limited to, nickel, palladium and/or platinum.

In a particular embodiment, the catalyst metal may be selected from the group consisting of a Group 8 metal, a Group 9 metal, a Group 10 metal and a combination thereof. Additionally or alternatively, the at least one catalyst metal may be selected from the group consisting of platinum (Pt), palladium (Pd), iridium (Ir), rhodium (Rh) or a combination thereof, particularly, platinum (Pt), palladium (Pd), and a mixture thereof.

Additionally or alternatively, the catalyst metal may be present in an amount of at least about 0.010 wt. %, at least about 0.050 wt. %, at least about 0.10 wt. %, at least about 0.20 wt. %, at least about 0.40 wt. %, at least about 0.50 wt. %, at least about 0.60 wt. %, at least about 0.80 wt. %, at least about 1.0 wt. %, at least about 1.2 wt. %, at least about 1.4 wt. %, at least about 1.5 wt. %, at least about 1.6 wt. %, at least about 1.8 wt. %, at least about 2.0 wt. %, at least about 2.2 wt. %, at least about 2.4 wt. %, at least about 2.6 wt. %, at least about 2.8 wt. %, at least about 3.0 wt. %, at least about 3.5 wt. %, or at least about 4.0 wt. %. All metals weight percents are on support. By "on support" it is meant that the percents are based on the weight of the support, i.e., the organosilica material support and optionally, binder material. For example, if the support were to weigh 100 grams, then 20 wt. % catalyst metal would mean that 20 grams of the catalyst metal was on the support.

Additionally or alternatively, the catalyst metal may be present in an amount of about 0.010 wt. % to about 4.0 wt. %, about 0.010 wt. % to about 3.5 wt. %, about 0.010 wt. % to about 3.0 wt. %, about 0.010 wt. % to about 2.8 wt. %, about 0.010 wt. % to about 2.6 wt. %, about 0.010 wt. % to about 2.4 wt. %, about 0.010 wt. % to about 2.2 wt. %, about 0.010 wt. % to about 2.0 wt. %, about 0.010 wt. % to about 1.8 wt. %, about 0.010 wt. % to about 1.6 wt. %, about 0.010 wt. % to about 1.5 wt. %, about 0.010 wt. % to about 1.4 wt. %, about 0.010 wt. % to at least about 1.2 wt. %, about 0.010 wt. % to about 1.0 wt. %, about 0.010 wt. % to about 0.80 wt. %, about 0.010 wt. % to about 0.60 wt. %, about 0.010 wt. % to about 0.50 wt. %, about 0.010 wt. % to about 0.40 wt. %, about 0.010 wt. % to about 0.20 wt. %, about 0.010 wt. % to about 0.10 wt. %, about 0.10 wt. % to about 4.0 wt. %, about 0.10 wt. % to about 3.5 wt. %, about 0.10 wt. % to about 3.0 wt. %, about 0.10 wt. % to about 2.8 wt. %, about 0.10 wt. % to about 2.6 wt. %, about 0.10 wt. % to about 2.4 wt. %, about 0.10 wt. % to about 2.2 wt. %, about 0.10 wt. % to about 2.0 wt. %, about 0.10 wt. % to about 1.8 wt. %, about 0.10 wt. % to about 1.6 wt. %, about 0.10 wt. % to about 1.5 wt. %, about 0.10 wt. % to about 1.4 wt. %, about 0.10 wt. % to at least about 1.2 wt. %, about 0.10 wt. % to about 1.0 wt. %, about 0.10 wt. % to about 0.80 wt. %, about 0.10 wt. % to about 0.60 wt. %, about 0.10 wt. % to about 0.50 wt. %, about 0.10 wt. % to about 0.40 wt. %, about 0.10 wt. % to about 0.20 wt. %, about 1.0 wt. % to about 4.0 wt. %, about 1.0 wt. % to about 3.5 wt. %, about 1.0 wt. % to about 3.0 wt. %, about 1.0 wt. % to about 2.8 wt. %, about 1.0 wt. % to about 2.6 wt. %, about 1.0 wt. % to about 2.4 wt. %, about 1.0 wt. % to about 2.2 wt. %, about 1.0 wt. % to about 2.0 wt. %, about 1.0 wt. % to about 1.8 wt. %, about 1.0 wt. % to about 1.6 wt. %, about 1.0 wt. % to about 1.5 wt. %, about 1.0 wt. % to about 1.4 wt. %, or about 1.0 wt. % to at least about 1.2 wt. %.

In particular, the catalyst metal may be present in an amount of about 0.010 wt. % to about 4.0 wt. %, about 0.05 wt. % to about 3.5 wt. %, about 0.1 wt. % to about 2.0 wt. %, or about 0.1 wt. % to about 1.4 wt. %.

The catalyst metal can be incorporated into the organosilica material support by any convenient method, such as by impregnation, by ion exchange, by complexation to surface sites or physically admixed with the organosilica material support. If the catalyst metal is to be impregnated into or exchanged onto the organosilica material support and optionally, binder, it may be done, for example, by treating the organosilica material support with a suitable ion containing the catalyst metal. If the catalyst metal is platinum, suitable platinum compounds include chloroplatinic acid, platinous chloride and various compounds containing the platinum amine complex. The catalyst metal may also be incorporated into, onto, or with the composited support and binder material by utilizing a compound(s) wherein the catalyst metal is present in the cation of the compound and/or compounds or in which it is present in the anion of the compound(s). It should be noted that both cationic and anionic compounds can be used. Non-limiting examples of suitable palladium or platinum compounds in which the metal is in the form of a cation or cationic complex are Pd(NH$_3$)$_4$Cl$_2$ or Pt(NH$_3$)$_4$Cl$_2$ are particularly useful, as are anionic complexes such as the vanadate and metatungstate ions. Cationic forms of other metals are also very useful since they may be exchanged onto the crystalline material or impregnated into it.

The catalyst metal so incorporated may be employed to promote any one of a number of catalytic tranformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof. In particular, the catalyst metal may be employed for aromatic hydrogenation and/or saturation.

II.C. Binder

In various aspects, the hydrogenation catalyst may further comprise a binder or be self-bound. Suitable binders, include but are not limited to active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be selected from the group consisting of active and inactive materials, inorganic materials, clays, alumina, silica, silica-alumina, titania, zirconia, or a combination thereof. Particularly, the binder may be silica-alumina, alumina and/or zirconia, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The catalysts described herein typically can comprise, in a composited form, a ratio of support material to binder material of about 100 parts support material to about zero parts binder material; about 99 parts support material to about 1 parts binder material; about 95 parts support material to about 5 parts binder material. Additionally or alternatively, the catalysts described herein typically can comprise, in a composited form, a ratio of support material to binder material ranging from about 90 parts support material to about 10 parts binder material to about 10 parts support material to about 90 parts binder material; about 85 parts support material to about 15 parts binder material to about 15 parts support material to about 85 parts binder material; about 80 parts support material to 20 parts binder material to 20 parts support material to 80 parts binder material, all ratios being by weight, typically from 80:20 to 50:50 support material:binder material, preferably from 65:35 to 35:65. Compositing may be done by conventional means including mulling the materials together followed by extrusion of pelletizing into the desired finished catalyst particles.

II.D. Further Metals

In some embodiments, the organosilica material support can further comprise cationic metal sites incorporated into the network structure. Such cationic metal sites may be incorporated by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Additionally or alternatively, the organosilica material support can further comprise a surface metal incorporated within the pores of the organosilica material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-10 and/or 13 elements may be present on an exterior and/or interior surface of the organosilica material support. For example, one or more of the Group 1, 2 and/or 13 elements may be present in a first layer on the organosilica material and one or more of the Group 6, 8, 9 and/or 10 elements may be present in a second layer, e.g., at least partially atop the Group 1, 2 and/or 13 elements. Additionally or alternatively, only one or more Group 6, 8, 9 and/or 10 elements may present on an exterior and/or interior surface of the organosilica material. The surface metal(s) can be incorporated into/onto the organosilica material by any convenient method, such as by impregnation, deposition, grafting, co-condensation, by ion exchange, and/or the like. In particular, a Group 13 metal, such as, but not limited to, aluminum may be grafted onto a surface of the organosilica material support. Additionally or alternatively, a Group 4 metal, such as, but not limited to, titanium, zirconium and hafnium, may be grafted onto a surface of the organosilica material support.

III. Methods of Making Hydrogenation Catalysts

In another embodiment, methods of producing the hydrogenation catalysts described herein for aromatic saturation are provided. The method comprises:

(a) providing an aqueous mixture that contains essentially no structure directing agent and/or porogen;

(b) adding at least one compound of Formula $[Z^{15}Z^{16}SiCH_2]_3$ (VII) into the aqueous mixture to form a solution, wherein each $Z^{15}$ can be a $C_1$-$C_4$ alkoxy group and each $Z^{16}$ can be a $C_1$-$C_4$ alkoxy group or a $C_1$-$C_4$ alkyl group;

(c) aging the solution to produce a pre-product; and (d) drying the pre-product to obtain an organosilica material support which is a polymer comprising independent units of a monomer of Formula $[Z^1OZ^2OSiCH_2]_3$ (I), as described herein; and (e) impregnating the organosilica material support with at least one catalyst metal selected from the group consisting of a Group 8 metal, a Group 9 metal, a Group 10 metal and a combination thereof.

Additionally or alternatively, the at least one compound of Formula $[Z^{15}Z^{16}SiCH_2]_3$ (VII) can be added in step (b) as at least partially hydroxylated and/or as at least partially polymerized/oligomerized, such that each $Z^{15}$ and/or $Z^{16}$ can more broadly represent a hydroxyl group, a $C_1$-$C_4$ alkoxy group, a $C_1$-$C_4$ alkyl group, or an oxygen atom bonded to a silicon atom of another siloxane. In other words, an unaged pre-product can be added in step (b), in addition to or as an alternative to the monomeric (at least one) compound of Formula $[Z^{15}Z^{16}SiCH_2]_3$ (VII) and yet still form the polymer in step (d).

III.A. Aqueous Mixture

The organosilica materials described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

1. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4))a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

2. Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyper-branched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

3. Base/Acid

In various embodiments, the aqueous mixture used in methods provided herein can comprise a base and/or an acid.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 9 to about 14 or about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

III.B. Compounds of Formula (VII)

The methods provided herein comprise the step of adding at least one compound of Formula $[Z^{15}Z^{16}SiCH_2]$ (VII) into the aqueous mixture to form a solution, wherein each $Z^{15}$ can be a $C_1$-$C_4$ alkoxy group and each $Z^{16}$ can be a $C_1$-$C_4$ alkoxy group or a $C_1$-$C_4$ alkyl group.

In one embodiment, each $Z^{15}$ can be a $C_1$-$C_3$ alkoxy or methoxy or ethoxy.

Additionally or alternatively, each $Z^{16}$ can be a $C_1$-$C_4$ alkoxy, a $C_1$-$C_3$ alkoxy or methoxy or ethoxy. Additionally or alternatively, each $Z^{16}$ can comprise methyl, ethyl or propyl, such as a methyl or ethyl.

Additionally or alternatively, each $Z^{15}$ can be a $C_1$-$C_2$ alkoxy group and $Z^{16}$ can be a $C_1$-$C_2$ alkoxy group or a $C_1$-$C_2$ alkyl group.

Additionally or alternatively, each $Z^{15}$ can be methoxy or ethoxy and each $Z^{16}$ can be methyl or ethyl.

In a particular embodiment, each $Z^{15}$ and $Z^{16}$ can be ethoxy, such that the compound corresponding to Formula (VII) can be 1,1,3,3,5,5-hexaethoxy-1,3,5-trisilacyclohexane, $([(EtO)_2SiCH_2]_3)$.

In a particular embodiment, each $Z^{15}$ can be ethoxy and each $Z^{16}$ can be methyl, such that compound corresponding to Formula (VII) can be 1,3,5-trimethyl-1,3,5-triethoxy-1,3,5-trisilacyclohexane, $([EtOCH_3SiCH_2]_3)$.

As mentioned hereinabove, the at least one compound of Formula (VII) can additionally or alternatively be at least partially hydroxylated and/or polymerized/oligomerized when added into the aqueous mixture to form a solution.

Additionally or alternatively, the method can further comprise adding to the aqueous mixture a further compound Formula (VII), which may be the same or different. In the case where different compounds of Formula (VII) are added, an organosilica material support can be obtained which is a copolymer comprising at least one independent unit of Formula (I) as described herein and at least one independent unit of Formulas (II) as described herein. For example, 1,1,3,3,5,5-hexaethoxy-1,3,5-trisilacyclohexane, $([(EtO)_2SiCH_2]_3)$ and 1,3,5-trimethyl-1,3,5-triethoxy-1,3,5-trisilacyclohexane, $([EtOCH_3SiCH_2]_3)$ may be added to the aqueous mixture.

When more than one compound of Formula (VII) is used, the respective compounds may be used in a wide variety of molar ratios. For example, if two compounds of Formula (VII) are used, the molar ratio of each compound may vary from 1:99 to 99:1, such as from 10:90 to 90:10. The use of different compounds of Formula (Ia) allows to tailor the properties of the organosilica materials made by the process of the invention, as will be further explained in the examples and in the section of this specification describing the properties of the organosilicas made by the present processes.

III.D. Compounds of Formula (VIII)

In additional embodiments, the methods provided herein can further comprise adding to the aqueous solution a compound of Formula $Z^{17}OZ^{18}Z^{19}Z^{20}Si$ (VIII) to obtain an organosilica material which is a copolymer comprising at least one independent unit of Formula (I) as described herein, at least one independent unit of Formula (III) as described herein and optionally at least one independent unit of Formula (II) as described herein, wherein each $Z^{17}$ can be a $C_1$-$C_6$ alkyl group, and $Z^{18}$, $Z^{19}$ and $Z^{20}$ each independently can be selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group.

Additionally or alternatively, each $Z^{17}$ can be a $C_1$-$C_6$ alkyl group, and $Z^{18}$, $Z^{19}$ and $Z^{20}$ each independently can be selected from the group consisting of a $C_1$-$C_6$ alkyl group and a $C_1$-$C_6$ alkoxy group. Additionally or alternatively, $Z^{18}$, $Z^{19}$ and $Z^{20}$ each independently optionally can be a nitrogen-containing $C_1$-$C_{10}$ alkyl group, a nitrogen-containing heteroaralkyl group, and a nitrogen-containing optionally substituted heterocycloalkyl group.

In various aspects, each $Z^{17}$ can be a $C_1$-$C_5$ alkyl group, a $C_1$-$C_4$ alkyl group, a $C_1$-$C_3$ alkyl group, a $C_1$-$C_2$ alkyl group, or methyl. In particular, $Z^{17}$ can be methyl or ethyl.

Additionally or alternatively, $Z^{18}$, $Z^{19}$ and $Z^{20}$ can be each independently a $C_1$-$C_5$ alkyl group, a $C_1$-$C_4$ alkyl group, a $C_1$-$C_3$ alkyl group, a $C_1$-$C_2$ alkyl group, or methyl.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group.

Additionally or alternatively, $Z^{18}$, $Z^{19}$ and $Z^{20}$ can be each independently a $C_1$-$C_5$ alkoxy group, a $C_1$-$C_4$ alkoxy group, a $C_1$-$C_3$ alkoxy group, a $C_1$-$C_2$ alkoxy group, or methoxy.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkoxy group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group or a $C_1$-$C_2$ alkoxy group.

Additionally or alternatively, $Z^{18}$, $Z^{19}$ and $Z^{20}$ can be each independently a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^{18}$, $Z^{19}$ and $Z^{20}$ can be each independently a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

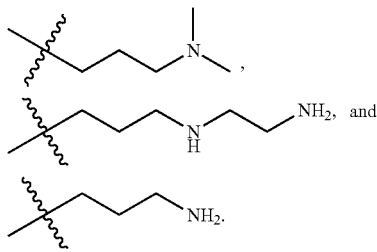

Additionally or alternatively, each $Z^{17}$ can be a $C_1$-$C_2$ alkyl group and $Z^{18}$, $Z^{19}$ and $Z^{20}$ can be each independently a nitrogen-containing $C_3$-$C_8$ alkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group or a nitrogen-containing $C_3$-$C_8$ alkyl group.

Additionally or alternatively, $Z^{18}$, $Z^{19}$ and $Z^{20}$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, each $Z^{17}$ can be a $C_1$-$C_2$ alkyl group and $Z^{18}$, $Z^{19}$ and $Z^{20}$ can be each independently a nitrogen-containing heteroaralkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_8$ alkyl group or a nitrogen-containing heteroaralkyl group.

Additionally or alternatively, $Z^{18}$, $Z^{19}$ and $Z^{20}$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, each $Z^{17}$ can be a $C_1$-$C_2$ alkyl group and $Z^{18}$, $Z^{19}$ and $Z^{20}$ can be each independently a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

In a particular embodiment, $Z^{17}$ can be ethyl and $Z^{18}$, $Z^{19}$ and $Z^{20}$ can be ethoxy, such that the compound corresponding to Formula (VIII) can be tetraethyl orthosilicate (TEOS) (($EtO)_4Si$).

In another particular embodiment, a compound of Formula (VII) can be 1,1,3,3,5,5-hexaethoxy-1,3,5-trisilacyclohexane ($[(EtO)_2SiCH_2]_3$) and a compound of Formula (VIII) can be tetraethyl orthosilicate (TEOS) (($EtO)_4Si$).

In another particular embodiment, $Z^{17}$ can be ethyl, $Z^{18}$ can be methyl and $Z^{19}$ and $Z^{20}$ can be ethoxy, such that the compound corresponding to Formula (VIII) can be methyltriethoxysilane (MTES) (($EtO)_3CH_3Si$).

In another particular embodiment, a compound of Formula (VII) can be 1,1,3,3,5,5-hexaethoxy-1,3,5-trisilacyclohexane ($[(EtO)_2SiCH_2]_3$) and a compound of Formula (VIII) can be methyltriethoxysilane (MTES) (($EtO)_3CH_3Si$).

In another particular embodiment, a compound of Formula (VII) can be 1,3,5-trimethyl-1,3,5-triethoxy-1,3,5- trisilacyclohexane ([EtOCH$_3$SiCH$_2$]$_3$ and a compound of Formula (VIII) can be tetraethyl orthosilicate (TEOS) ((EtO)$_4$Si).

In another particular embodiment, $Z^{17}$ can be ethyl, $Z^{18}$ and $Z^{19}$ can be ethoxy and $Z^{20}$ can be

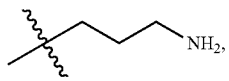

such that the compound corresponding to Formula (VIII) can be (3-aminopropyl)triethoxysilane (H$_2$N(CH$_2$)$_3$(EtO)$_3$Si).

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (VIII) can be (3-aminopropyl)triethoxysilane (H$_2$N(CH$_2$)$_3$(EtO)$_3$Si).

In another particular embodiment, $Z^{17}$ can be methyl, $Z^{18}$ and $Z^{19}$ can be methoxy and $Z^{20}$ can be

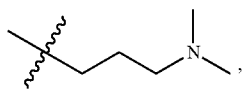 [SMILES: *CCCN(C)C]

such that the compound corresponding to Formula (VIII) can be (N,N-dimethylaminopropyl)trimethoxysilane (((CH$_3$)$_2$N(CH$_2$)$_3$)(MeO)$_3$Si).

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (VIII) can be (N,N-dimethylaminopropyl)trimethoxysilane (((CH$_3$)$_2$N(CH$_2$)$_3$)(MeO)$_3$Si).

In another particular embodiment, $Z^{17}$ can be ethyl, $Z^{18}$ and $Z^{19}$ can be ethoxy and $Z^{20}$ can be

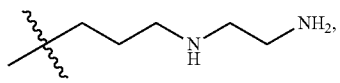 [SMILES: *CCCNCCN]

such that the compound corresponding to Formula (VIII) can be (N-(2-aminoethyl)-3-aminopropyltriethoxysilane ((H$_2$N(CH$_2$)$_2$NH (CH$_2$)$_3$)(EtO)$_2$Si).

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (VIII) can be (N-(2-aminoethyl)-3-aminopropyltriethoxysilane ((H$_2$N(CH$_2$)$_2$NH(CH$_2$)$_3$)(EtO)$_2$Si).

In another particular embodiment, $Z^{17}$ can be ethyl, $Z^{18}$ and $Z^{19}$ can be ethoxy and $Z^{20}$ can be

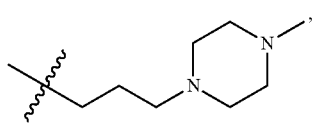 [SMILES: *CCCN1CCN(C)CC1]

such that the compound corresponding to Formula (VIII) can be 4-methyl-1-(3-triethoxysilylpropyl)-piperazine.

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (VIII) can be 4-methyl-1-(3-triethoxysilylpropyl)-piperazine.

In another particular embodiment, $Z^{17}$ can be ethyl, $Z^{18}$ and $Z^{19}$ can be ethoxy and $Z^{20}$ can be

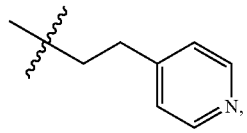

such that the compound corresponding to Formula (VIII) can be 4-(2-(triethoxysily)ethyl)pyridine.

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (VIII) can be 4-(2-(triethoxysily)ethyl)pyridine.

In another particular embodiment, $Z^{17}$ can be ethyl, $Z^{18}$ and $Z^{19}$ can be ethoxy and $Z^{20}$ can be

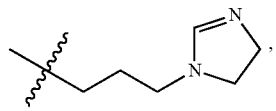 [SMILES: *CCCN1C=NCC1]

such that the compound corresponding to Formula (Va) can be 1-(3-(triethoxysilyl)propyl)-4,5-dihydro-1H-imidazole.

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (VIII) can be 1-(3-(triethoxysilyl)propyl)-4,5-dihydro-1H-imidazole.

The molar ratio of compound of Formula (VII) to compound of Formula (VIII) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (II) can be from about 4:1 to 1:4 or from about 2.5:1 to about 1:2.5, about 2:1 to about 1:2, such as about 1.5:1 to about 1.5:1.

III.D. Compounds of Formula (IX)

In additional embodiments, the methods provided herein can further comprise adding to the aqueous solution a compound of Formula $Z^{21}Z^{22}Z^{23}$Si—R$^1$—Si $Z^{21}Z^{22}Z^{23}$ (IX) to obtain an organosilica material which is a copolymer comprising at least one independent unit Formula (I) as described herein, at least one independent unit of Formula (IV) as described herein and optionally at least one independent unit of Formulas (II) and/or (III) as described herein, wherein each $Z^{21}$ independently can be a C$_1$-C$_4$ alkoxy group; each $Z^{22}$ and $Z^{23}$ independently can be a C$_1$-C$_4$ alkoxy group or a C$_1$-C$_4$ alkyl group; and each R$^1$ can be selected from the group consisting a C$_1$-C$_8$ alkylene group, a C$_2$-C$_8$ alkenylene group, a C$_2$-C$_8$ alkynylene group, a nitrogen-containing C$_2$-C$_{10}$ alkylene group, an optionally substituted C$_6$-C$_{20}$ aralkyl group, and an optionally substituted C$_4$-C$_{20}$ heterocycloalkyl group.

Additionally or alternatively, each $Z^{21}$ independently can be a C$_1$-C$_4$ alkoxy group; each $Z^{22}$ and $Z^{23}$ independently can be a C$_1$-C$_4$ alkoxy group or a C$_1$-C$_4$ alkyl group; and each R$^1$ can be selected from the group consisting a C$_1$-C$_8$ alkylene group, a C$_2$-C$_8$ alkenylene group, and a C$_2$-C$_8$ alkynylene group. Additionally or alternatively, R$^1$ can optionally be a nitrogen-containing C$_1$-C$_{10}$ alkylene group, an optionally substituted $C_6$-$C_{20}$ aralkyl group, and/or an optionally substituted $C_4$-$C_{20}$ heterocycloalkyl group.

In various embodiments, each $Z^{21}$ can be a $C_1$-$C_3$ alkoxy group, a $C_1$-$C_2$ alkoxy group, or methoxy.

Additionally or alternatively, each $Z^{22}$ and $Z^{23}$ independently can be a $C_1$-$C_3$ alkoxy group, a $C_1$-$C_2$ alkoxy group, or methoxy.

Additionally or alternatively, each $Z^{21}$ can be a $C_1$-$C_2$ alkoxy group and each $Z^{22}$ and $Z^{23}$ independently can be a $C_1$-$C_2$ alkoxy group.

Additionally or alternatively, each $Z^{22}$ and $Z^{23}$ independently can be a $C_1$-$C_3$ alkyl group, a $C_1$-$C_2$ alkyl group, or methyl.

Additionally or alternatively, each $Z^{21}$ can be a $C_1$-$C_2$ alkoxy group and each $Z^{22}$ and $Z^{23}$ independently can be a $C_1$-$C_2$ alkyl group.

Additionally or alternatively, $Z^{21}$ can be a $C_1$-$C_2$ alkoxy group and each $Z^{22}$ and $Z^{23}$ independently can be a $C_1$-$C_2$ alkoxy group or a $C_1$-$C_2$ alkyl group.

Additionally or alternatively, each $R^1$ can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —$CH_2$—.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^7$ can be a $C_1$-$C_2$ alkylene group.

Additionally or alternatively, each $R^1$ can be a $C_2$-$C_7$ alkenylene group, a $C_1$-$C_6$ alkenylene group, a $C_2$-$C_5$ alkenylene group, a $C_2$-$C_4$ a alkenylene group, a $C_2$-$C_3$ alkenylene group, or —CH=CH—.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^1$ can be a $C_1$-$C_2$ alkenylene group.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^1$ can be a $C_1$-$C_2$ alkylene group or a $C_1$-$C_2$ alkenylene group.

Additionally or alternatively, each $R^1$ can be a $C_2$-$C_7$ alkynylene group, a $C_1$-$C_6$ alkynylene group, a $C_2$-$C_5$ alkynylene group, a $C_2$-$C_4$ a alkynylene group, a $C_2$-$C_3$ alkynylene group, or —C≡C—.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and $R^1$ can be a $C_2$-$C_4$ alkynylene group.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group or a $C_2$-$C_4$ alkynylene group.

Additionally or alternatively, each $R^1$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen-containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

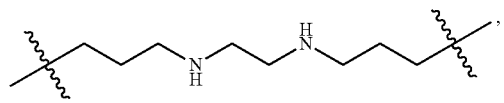

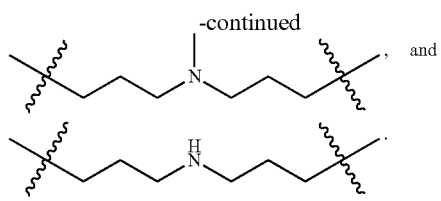

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^1$ can be a nitrogen-containing $C_4$-$C_{10}$ alkylene group.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group or a nitrogen-containing $C_4$-$C_{10}$ alkylene group.

Additionally or alternatively, each $R^1$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^1$ can be an optionally substituted $C_6$-$C_{10}$ aralkyl.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group, or an optionally substituted $C_6$-$C_{10}$ aralkyl.

Additionally or alternatively, $R^1$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and $R^1$ can be an optionally substituted $C_4$-$C_{12}$ heterocycloalkyl group.

Additionally or alternatively, each $Z^{21}$ can be a $C_1$-$C_2$ alkoxy group; each $Z^{22}$ and $Z^{23}$ independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group, an optionally substituted $C_6$-$C_{10}$ aralkyl, or an optionally substituted $C_4$-$C_{12}$ heterocycloalkyl group.

In a particular embodiment, each $Z^{21}$ and $Z^{22}$ can be ethoxy, each $Z^{23}$ can be methyl and $R^1$ can be —$CH_2CH_2$—, such that compound corresponding to Formula (IX) can be 1,2-bis(methyldiethoxysilyl)ethane ($CH_3(EtO)_2Si$—$CH_2CH_2$—$Si(EtO)_2CH_3$).

In another particular embodiment, a compound of Formula (VII) can be 1,1,3,3,5,5-hexaethoxy-1,3,5-trisilacyclohexane ([(EtO)$_2$SiCH$_2$]$_3$), and a compound of Formula (IX) can be 1,2-bis(methyldiethoxysilyl)ethane (CH$_3$(EtO)$_2$Si—CH$_2$CH$_2$—Si(EtO)$_2$CH$_3$).

In another particular embodiment, each $Z^{21}$, $Z^{22}$ and $Z^{23}$ can be ethoxy and R$^1$ can be —CH$_2$—, such that compound corresponding to Formula (IX) can be bis(triethoxysilyl)methane ((EtO)$_3$Si—CH$_2$—Si(EtO)$_3$).

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (IX) can be bis(triethoxysilyl)methane ((EtO)$_3$Si—CH$_2$—Si(EtO)$_3$).

In another particular embodiment, each $Z^{21}$, $Z^{22}$ and $Z^{23}$ can be ethoxy and R$^1$ can be —HC═CH—, such that compound corresponding to Formula (IX) can be 1,2-bis(triethoxysilyl)ethylene ((EtO)$_3$Si—HC═CH—Si(EtO)$_3$).

In another particular embodiment, a compound of Formula (VII) can be 1,1,3,3,5,5-hexaethoxy-1,3,5-trisilacyclohexane ([(EtO)$_2$SiCH$_2$]$_3$)) and a compound of Formula (IX) can be 1,2-bis(triethoxysilyl)ethylene ((EtO)$_3$Si—HC═CH—Si(EtO)$_3$).

In another particular embodiment, a compound of Formula (IX) can be bis(triethoxysilyl)methane ((EtO)$_3$Si—CH$_2$—Si(EtO)$_3$) and a compound of Formula (VIII) can be tetraethyl orthosilicate (TEOS) ((EtO)$_4$Si).

In a particular embodiment, each $Z^{21}$, $Z^{22}$ and $Z^{23}$ can be methoxy and R$^1$ can be

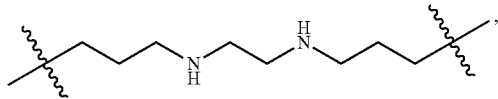 [SMILES: *CCCNCCNCCC*]

such that compound corresponding to Formula (IX) can be N,N'-bis[(3-trimethoxysilyl)propyl]ethylenediamine.

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (IX) can be N,N'-bis[(3-trimethoxysilyl)propyl]ethylenediamine.

In another particular embodiment, each $Z^{21}$ and $Z^{22}$ can be ethoxy, each $Z^{23}$ can be methyl and R$^1$ can be

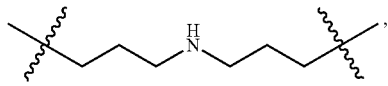 [SMILES: *CCCNCCC*]

such that compound corresponding to Formula (IX) can be bis[(methyldiethoxysilyl)propyl]amine.

In another particular embodiment, Formula (VII) can be 1,1,3,3,5,5-hexaethoxy-1,3,5-trisilacyclohexane ([(EtO)$_2$SiCH$_2$]$_3$) and a compound of Formula (IX) can be bis[(methyldiethoxysilyl)propyl]amine.

In another particular embodiment, each $Z^{21}$ and $Z^{22}$ can be methoxy, each $Z^{23}$ can be methyl and R$^1$ can be

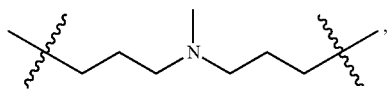 [SMILES: *CCCN(C)CCC*]

such that compound corresponding to Formula (IX) can be bis[(methyldimethoxysilyl)propyl]-N-methylamine.

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (IX) can be bis[(methyldimethoxysilyl)propyl]-N-methylamine and optionally, no other compounds are added to the aqueous mixture.

The molar ratio of compound of Formula (VII) to compound of Formula (IX) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (III) can be from about 4:1 to 1:4 or from about 2.5:1 to 1:2.5, about 2:1 to about 1:2, such as about 1.5:1 to about 1.5:1.

III.E. Sources of Trivalent Metal Oxide

In additional embodiments, the methods provided herein can comprise adding to the aqueous solution a source of a trivalent metal oxide.

Sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, Al$_2$O$_3$, aluminum halides (e.g., AlCl$_3$), NaAlO$_2$, boron nitride, B$_2$O$_3$ and/or H$_3$BO$_3$.

In various aspects, the source of trivalent metal oxide may be a compound of Formula M$^3$(OZ$^{24}$)$_3$ (X) to obtain an organosilica material which is a copolymer comprising at least one independent unit Formula (I) as described herein, at least one independent unit of Formula (V) as described herein and optionally at least one independent unit of Formulas (II), (III) and/or (IV) as described herein, wherein M$^3$ can be a Group 13 metal and each Z$^{24}$ independently can be a C$_1$-C$_6$ alkyl group.

In one embodiment, M$^3$ can be B, Al, Ga, In, Il, or Uut. In particular, M$^3$ can be Al or B.

Additionally or alternatively, each Z$^{24}$ can be a C$_1$-C$_6$ alkyl group, a C$_1$-C$_5$ alkyl group, a C$_1$-C$_4$ alkyl group, a C$_1$-C$_3$ alkyl group, a C$_1$-C$_2$ alkyl group or methyl. In particular, Z$^{15}$ can be methyl, ethyl, propyl or butyl.

Additionally or alternatively, M$^3$ can be Al or B and each Z$^{24}$ can be methyl, ethyl, propyl or butyl.

In a particular embodiment, M$^3$ can be Al and each Z$^{24}$ can be methyl, such that compound corresponding to Formula (X) can be aluminum trimethoxide.

In a particular embodiment, M$^3$ can be Al and each Z$^{24}$ can be ethyl, such that compound corresponding to Formula (X) can be aluminum triethoxide.

In a particular embodiment, M$^3$ can be Al and each Z$^{24}$ can be propyl, such that compound corresponding to Formula (X) can be aluminum isopropoxide.

In a particular embodiment, M$^3$ can be Al and each Z$^{24}$ can be butyl, such that compound corresponding to Formula (X) can be aluminum tri-sec-butoxide.

In another particular embodiment, a compound of Formula (VII) can be 1,1,3,3,5,5-hexaethoxy-1,3,5-trisilacyclohexane, ([(EtO)$_2$SiCH$_2$]$_3$) and a compound of Formula (X) can be selected from the group consisting of aluminum trimethoxide, aluminum triethoxide, aluminum isopropoxide, and aluminum tri-sec-butoxide.

In another particular embodiment, a compound of Formula (VII) can be 1,1,3,3,5,5-hexaethoxy-1,3,5-trisilacyclohexane, ([(EtO)$_2$SiCH$_2$]$_3$) and a compound of Formula (X) can be aluminum tri-sec-butoxide.

Additionally or alternatively, the source of trivalent metal oxide may be a compound of Formula (Z$^{25}$O)$_2$M$^4$-O—Si(OZ$^{26}$)$_3$ (XI) to obtain an organosilica material which is a copolymer comprising at least one independent unit Formula (I) as described herein, at least one independent unit of Formula (VI) as described herein and optionally at least one independent unit of Formulas (II), (III), (IV) and/or (V) as described herein, wherein $M^4$ can be a Group 13 metal and each $Z^{25}$ and each $Z^{26}$ each independently can be a $C_1$-$C_6$ alkyl group.

In one embodiment, $M^4$ can be B, Al, Ga, In, Il, or Uut. In particular, $M^4$ can be Al or B.

Additionally or alternatively, each $Z^{25}$ and each $Z^{26}$ independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, each $Z^{25}$ and each $Z^{26}$ independently can be methyl, ethyl, propyl or butyl.

Additionally or alternatively, $M^4$ can be Al or B and each $Z^{25}$ and each $Z^{26}$ independently can be methyl, ethyl, propyl or butyl.

Additionally or alternatively, the source of a trivalent metal oxide may be a source of a compound of Formula (X) (e.g., $AlCl_3$), and/or a source of a compound of Formula (XI).

III.F. Metal Chelate Sources

In additional embodiments, the methods provided herein can further comprise adding to the aqueous solution a source of metal chelate compounds.

Examples of metal chelate compounds, when present, can include titanium chelate compounds such as triethoxy.mono(acetylacetonato) titanium, tri-n-propoxy.mono(acetylacetonato)titanium, tri-i-propoxy.mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, diethoxy.bis(acetylacetonato)titanium, di-n-propoxy.bis(acetylacetonato)titanium, di-i-propoxy.bis(acetylacetonato)titanium, di-n-butoxy.bis(acetylacetonato) titanium, di-sec-butoxy.bis(acetylacetonato)titanium, di-t-butoxy.bis(acetylacetonato)titanium, monoethoxy.tris(acetylacetonato)titanium, mono-n-propoxy.tris(acetylacetonato)titanium, mono-i-propoxy.tris(acetylacetonato)titanium, mono-n-butoxy.tris(acetylacetonato)titanium, mono-sec-butoxy.tris(acetylacetonato)titanium, mono-t-butoxy-tris(acetylacetonato)titanium, tetrakis(acetylacetonato)titanium, triethoxy.mono(ethylacetoacaato)titanium, tri-n-propoxy.mono(ethylacetoacetato)titanium, tri-i-propoxy.mono(ethylacetoacetato) titanium, tri-n-butoxy.mono(ethylacetoacetato)titanium, tri-sec-butoxy.mono(ethylacetoacetato) titanium, tri-t-butoxy-mono(ethylacetoacetato)titanium, diethoxy.bis(ethylacetoacetato)titanium, di-n-propoxy.bis(ethylacetoacetato)titanium, di-i-propoxy.bis(ethylacetoacetato)titanium, di-n-butoxy.bis(ethylacetoacetato)titanium, di-sec-butoxy.bis(ethylacetoacetato)titanium, di-t-butoxy.bis(ethylacetoacetato)titanium, monoethoxy.tris(ethylacetoacetato)titanium, mono-n-propoxy.tris(ethylacetoacetato)titanium, mono-i-propoxy.tris(ethylacetoaetato)titanium, mono-n-butoxy.tris(ethylacetoacetato)titanium, mono-sec-butoxy.tris(ethylacetoacetato)titanium, mono-t-butoxy.tris(ethylacetoacetato)titanium, tetrakis(ethylacetoacetato) titanium, mono(acetylacetonato)tris(ethylacetoacetato) titanium, bis(acetylacetonato)bis(ethylacetoacetato) titanium, and tris(acetylacetonato)mono(ethylacetoacetato) titanium; zirconium chelate compounds such as triethoxy.mono(acetylacetonato)zirconium, tri-n-propoxy.mono(acetylacetonato) zirconium, tri-i-propoxy.mono(acetylacetonato)zirconium, tri-n-butoxy.mono(acetylacetonato)zirconium, tri-sec-butoxy.mono(acetylacetonato) zirconium, tri-t-butoxy.mono(acetylacetonato)zirconium, diethoxy.bis(acetylacetonato)zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, monoethoxy.tris(acetylacetonato)zirconium, mono-n-propoxy.tris(acetylacetonato)zirconium, mono-i-propoxy.tris(acetylacetonato)zirconium, mono-n-butoxy.tris(acetylacetonato)zirconium, mono-sec-butoxy.tris(acetylacetonato)zirconium, mono-t-butoxy.tris(acetylacetonato)zirconium, tetrakis(acetylacetonato)zirconium, triethoxy.mono(ethylacetoacetato)zirconium, tri-n-propoxy.mono(ethylacetoacetato)zirconium, tri-i-propoxy.mono(ethylacetoacetato)zirconium, tri-n-butoxy.mono(ethylacetoacetato)zirconium, tri-sec-butoxy.mono(ethylacetoacetato)zirconium, tri-t-butoxy.mono(ethylacetoacetato)zirconium, diethoxy.bis(ethylacetoacetato)zirconium, di-n-propoxy.bis(ethylacetoacetato)zirconium, di-i-propoxy.bis(ethylacetoacetato)zirconium, di-n-butoxy.bis(ethylacetoacetato) zirconium, di-sec-butoxy.bis(ethylacetoacetato)zirconium, di-t-butoxy.bis(ethylacetoacetato)zirconium, monoethoxy.tris(ethylacetoacetato)zirconium, mono-n-propoxy.tris(ethylacetoacetato)zirconium, mono-i-propoxy.tris(ethylacetoacetato)zirconium, mono-n-butoxy.tris(ethylacetoacetato)zirconium, mono-sec-butoxy.tris(ethylacetoacetato)zirconium, mono-t-butoxy.tris(ethylacetoacetato)zirconium, tetrakis(ethylacetoacetato) zirconium, mono(acetylacetonato)tris(ethylacetoacetato) zirconium, bis(acetylacetonato)bis(ethylacetoacetato) zirconium, and tris(acetylacetonato)mono(ethylacetoacetato)zirconium; and aluminum chelate compounds such as tris(acetylacetonato)aluminum and tris (ethylacetoacetato)aluminum. Of these, the chelate compounds of titanium or aluminum can be of note, of which the chelate compounds of titanium can be particularly of note. These metal chelate compounds may be used either singly or in combination.

III.G. Molar Ratio

In the methods described herein, a molar ratio of Formula (VII):Formula (VII), Formula (VII):Formula (VIII), Formula (VII):Formula (IX), Formula (IX):Formula (VIII), Formula (VII):Formula (X), and Formula (VII):Formula (XI) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1 about 5:2 and about 15:1 may be used. For example, a molar ratio of Formula (VII):Formula (VII) can be about 3:2. A molar ratio of Formula (VII):Formula (VIII) can be about 2:3, about 4:3, about 4:1 or about 3:2. A molar ratio of Formula (VII):Formula (IX) can be about 2:3, and about 4:1. A molar ratio of Formula (IX):Formula (VIII) can be about 5:2, about 1:1, about 1:2 or about 2:3. A molar ratio of Formula (VII):Formula (X) and Formula (VII):Formula (XI) can be about 15:1 or about 5:1.

III.H. Aging the Solution

The solution formed in the methods described herein can be aged for at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days) or at least about 144 hours (6 days).

Additionally or alternatively, the solution formed in the methods described herein can be aged for about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours (1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours (3 days) to about 144 hours (6 days), about 72 hours (3 days) to about 120 hours (5 days), about 72 hours (3 days) to about 96 hours (4 days), about 96 hours (4 days) to about 144 hours (6 days), about 96 hours (4 days) to about 120 hours (5 days), or about 120 hours (5 days) to about 144 hours (6 days).

Additionally or alternatively, the solution formed in the method can be aged at temperature of at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C. at least about 130° C., at least about 140° C., at least about 150° C., at least about 175° C., at least about 200° C., at least about 250° C., or about 300° C.

Additionally or alternatively, the solution formed in the method can be aged at temperature of about 10° C. to about 300° C., about 10° C. to about 250° C., about 10° C. to about 200° C., about 10° C. to about 175° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 20° C. to about 300° C., about 20° C. to about 250° C., about 20° C. to about 200° C., about 20° C. to about 175° C., about 20° C. to about 150° C., about 20° C. to about 140° C., about 20° C. to about 130° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 30° C. to about 300° C., about 30° C. to about 250° C., about 30° C. to about 200° C., about 30° C. to about 175° C., about 30° C. to about 150° C., about 30° C. to about 140° C., about 30° C. to about 130° C., about 30° C. to about 120° C., about 30° C. to about 110° C., about 30° C. to about 100° C., about 30° C. to about 90° C., about 30° C. to about 80° C., about 30° C. to about 70° C., about 30° C. to about 60° C., about 30° C. to about 50° C., about 50° C. to about 300° C., about 50° C. to about 250° C., about 50° C. to about 200° C., about 50° C. to about 175° C., about 50° C. to about 150° C., about 50° C. to about 140° C., about 50° C. to about 130° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 70° C. to about 300° C., about 70° C. to about 250° C., about 70° C. to about 200° C., about 70° C. to about 175° C., about 70° C. to about 150° C., about 70° C. to about 140° C., about 70° C. to about 130° C., about 70° C. to about 120° C., about 70° C. to about 110° C., about 70° C. to about 100° C., about 70° C. to about 90° C., about 70° C. to about 80° C., about 80° C. to about 300° C., about 80° C. to about 250° C., about 80° C. to about 200° C., about 80° C. to about 175° C., about 80° C. to about 150° C., about 80° C. to about 140° C., about 80° C. to about 130° C., about 80° C. to about 120° C., about 80° C. to about 110° C., about 80° C. to about 100° C., about 80° C. to about 90° C., about 90° C. to about 300° C., about 90° C. to about 250° C., about 90° C. to about 200° C., about 90° C. to about 175° C., about 90° C. to about 150° C., about 90° C. to about 140° C., about 90° C. to about 130° C., about 90° C. to about 120° C., about 90° C. to about 110° C., about 90° C. to about 100° C., about 100° C. to about 300° C., about 100° C. to about 250° C., about 100° C. to about 200° C., about 100° C. to about 175° C., about 100° C. to about 150° C., about 100° C. to about 140° C., about 100° C. to about 130° C., about 100° C. to about 120° C., about 100° C. to about 110° C., about 110° C. to about 300° C., about 110° C. to about 250° C., about 110° C. to about 200° C., about 110° C. to about 175° C., about 110° C. to about 150° C., about 110° C. to about 140° C., about 110° C. to about 130° C., about 110° C. to about 120° C., about 120° C. to about 300° C., about 120° C. to about 250° C., about 120° C. to about 200° C., about 120° C. to about 175° C., about 120° C. to about 150° C., about 120° C. to about 140° C., about 120° C. to about 130° C., about 130° C. to about 300° C., about 130° C. to about 250° C., about 130° C. to about 200° C., about 130° C. to about 175° C., about 130° C. to about 150° C., or about 130° C. to about 140° C.

III.I. Drying the Pre-Product

The methods described herein comprise drying the pre-product (e.g., a gel) to produce an organosilica material support.

In some embodiments, the pre-product (e.g., a gel) formed in the method can be dried at a temperature of greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the pre-product (e.g., a gel) formed in the method can be dried at temperature of about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 110° C., about 70° C. to about 100° C., about 70° C. to about 80° C., about 80° C. to about 600° C., about 80° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C.

In a particular embodiment, the pre-product (e.g., a gel) formed in the method can be dried at temperature from about 70° C. to about 200° C.

Additionally or alternatively, the pre-product (e.g., a gel) formed in the method can be dried in a $N_2$ and/or air atmosphere.

III.J. Catalyst Metal Impregnation

In additional embodiments, the methods of making a hydrogenation catalyst can further comprise impregnating the organosilica material support with at least one catalyst metal as described herein. In particular, the at least one catalyst metal can be selected from the group consisting of a Group 6 element, a Group 8 element, a Group 9 element, a Group 10 element or a combination thereof, particularly a Group 8, 9, and/or 10 metal (e.g., Pt, Pd, Ir, Rh, Os or a combination thereof). In an alternative preferred embodiment, the metal hydrogenation component can be a combination of a non-noble Group VIII metal with a Group VI metal. Suitable combinations can include Ni, Co, or Fe with Mo or W, preferably Ni with Mo or W. The organosilica material support may be impregnated with the catalyst metal by incipient wetness or ion exchanged.

Additionally or alternatively, the catalyst metal may be incorporated into the hydrogenation catalyst by complexation to surface sites, or during mullmixing.

III.K. Addition of Binder

In additional embodiments, the methods of making a hydrogenation catalyst can further comprise adding a binder material as described herein. In particular, the binder material may be selected from the group consisting of active and inactive materials, inorganic materials, clays, alumina, silica, silica-alumina, titania, zirconia, or a combination thereof. Particularly, the binder may be silica-alumina, alumina and/or zirconia.

III.L. Further Metals

In additional embodiments, the methods of making a hydrogenation catalyst can further comprise adding a surface metal as described herein incorporated within the pores of the organosilica material support. Addition of the surface metal can occur prior to impregnation of organosilica material support with the catalyst material. The surface metal can be selected from a Group 1 element, a Group 2 element, a Group 13 element, and a combination thereof as described above. Additionally or alternatively, sources of the surface metal may be compounds of Formulas (X) and/or (XI) as described herein. In particular, the methods described herein can further comprise grafting aluminum on a surface of the organosilica material support prior to impregnating the organosilica material support.

III.M. Optional Further Steps

In some embodiments, the method can further comprise calcining the organosilica material support to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 400° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 400° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

IV. Hydrogenation Catalyst Product-By-Process

Hydrogenation catalysts can be made from the methods described herein. In another particular embodiment, hydrogenation catalysts can be made from an aqueous mixture as described herein that contains essentially no structure directing agent or porogen as described herein to form an organosilica material support as described herein and at least one catalyst metal as described herein, wherein the organosilica material support may be:
(i) a homopolymer comprising units of Formula (I) as described herein; or
(ii) a copolymer comprising independent units of Formula (I) as described herein and at least one other monomer comprising units of Formulas (II) (III), (IV), (V), and/or (VI) as described herein.

V. Aromatic Hydrogenation Process

In various embodiments, an aromatics hydrogenation process for a hydrocarbon feedstream is provided herein. The aromatics hydrogenation process can comprise contacting a hydrocarbon feedstream comprising aromatics with a hydrogenation catalyst as described herein in the presence of a hydrogen-containing treat gas in a first reaction stage operated under effective aromatics hydrogenation conditions to produce a reaction product with reduced aromatics content. As understood herein, a hydrogenation catalyst can be used for both hydrogenation and aromatic saturation of a feedstream. Similarly, a hydrogenation process can refer to either hydrogenation or aromatic saturation of a feedstream.

In various embodiments, the hydrogenation process can be achieved by contacting a hydrocarbon feedstream with a hydrogenation catalyst described herein in the presence of a hydrogen-containing treat gas in a first reaction stage operated under effective aromatics hydrogenation conditions to produce a reaction product with reduced aromatics content.

Hydrogen-containing treat gasses suitable for use in a hydrogenation process can be comprised of substantially pure hydrogen or can be mixtures of other components typically found in refinery hydrogen streams. It is preferred that the hydrogen-containing treat gas stream contains little, more preferably no, hydrogen sulfide. The hydrogen-containing treat gas purity should be at least about 50% by volume hydrogen, preferably at least about 75% by volume hydrogen, and more preferably at least about 90% by volume hydrogen for best results. It is most preferred that the hydrogen-containing stream be substantially pure hydrogen.

Feedstreams suitable for hydrogenation by the hydrogenation catalyst described herein include any conventional hydrocarbon feedstreams where hydrogenation or aromatic saturation is desirable. Typically, an input feed for an aromatic saturation process can be generated as a product or side-product from a previous type of hydroprocessing, such as hydrocracking for fuels or lubricant base stock production. A wide range of petroleum and chemical feedstocks can be hydroprocessed. Such feedstreams can include hydrocarbon fluids, diesel, kerosene, lubricating oil feedstreams, heavy coker gasoil (HKGO), de-asphalted oil (DAO), FCC main column bottom (MCB), steam cracker tar. Such feedstreams can also include other distillate feedstreams such as light to heavy distillates including raw virgin distillates, wax-containing feedstreams such as feeds derived from crude oils, shale oils and tar sands. Synthetic feeds such as those derived from the Fischer-Tropsch process can also be aromatically saturated using the hydrogenation catalyst described herein. Typical wax-containing feedstocks for the preparation of lubricating base oils have initial boiling points of about 315° C. or higher, and include feeds such as whole and reduced petroleum crudes, hydrocrackates, raffinates, hydrotreated oils, gas oils (such as atmospheric gas oils, vacuum gas oils, and coker gas oils), atmospheric and vacuum residues, deasphalted oils/residua (e.g., propane deasphalted residua, brightstock, cycle oil), dewaxed oils, slack waxes and Fischer-Tropsch wax, and mixtures of these materials. Such feeds may be derived from distillation towers (atmospheric and vacuum), hydrocrackers, hydrotreaters and solvent extraction units, and may have wax contents of up to 50% or more. Preferred lubricating oil boiling range feedstreams include feedstreams which boil in the range of 650-1100° F. Diesel boiling range feedstreams include feedstreams which boil in the range of 480-660° F. Kerosene boiling range feedstreams include feedstreams which boil in the range of 350-617° F.

Hydrocarbon feedstreams suitable for use herein also contain aromatics and nitrogen- and sulfur-contaminants. Feedstreams containing up to 0.2 wt. % of nitrogen, based on the feedstream, up to 3.0 wt. % of sulfur, and up to 50 wt. % aromatics can be used in the present process In various embodiments, the sulfur content of the feedstreams can be below about 500 wppm, or below about 300 wppm, or below about 200 wppm, or below about 100 wppm, or below about 50 wppm, or below about 15 wppm. The pressure used during an aromatic hydrogenation process can be modified based on the expected sulfur content in a feedstream. Feeds having a high wax content typically have high viscosity indexes of up to 200 or more. Sulfur and nitrogen contents may be measured by standard ASTM methods D2622 (sulfur), and D5453 and/or D4629 (nitrogen), respectively.

Effective hydrogenation conditions may be considered to be those conditions under which at least a portion of the aromatics present in the hydrocarbon feedstream are saturated, preferably at least about 50 wt. % of the aromatics are saturated, more preferably greater than about 75 wt. %. Effective hydrogenation conditions can include temperatures of from 150° C. to 400° C., a hydrogen partial pressure of from 740 to 20786 kPa (100 to 3000 psig), a space velocity of from 0.1 to 10 liquid hourly space velocity (LHSV), and a hydrogen to feed ratio of from 89 to 1780 m$^3$/m$^3$ (500 to 10000 scf/B).

Additionally or alternatively, effective hydrogenation conditions may be conditions effective at removing at least a portion of the nitrogen and organically bound sulfur contaminants and hydrogenating at least a portion of said aromatics, thus producing at least a liquid lube boiling range product having a lower concentration of aromatics and nitrogen and organically bound sulfur contaminants than the lube boiling range feedstream.

Additionally or alternatively, effective hydrogenation conditions may be conditions effective at removing at least a portion of the nitrogen and organically bound sulfur contaminants and hydrogenating at least a portion of said aromatics, thus producing at least a liquid diesel boiling range product having a lower concentration of aromatics and nitrogen and organically bound sulfur contaminants than the diesel boiling range feedstream.

As stated above, in some instances, the hydrocarbon feedstream (e.g., lube oil boiling range) may be hydrotreated to reduce the sulfur contaminants to below about 500 wppm, particularly below about 300 wppm, particularly below about 200 wppm or particularly below about 100 wppm. In such an embodiment, the process may comprise at least two reaction stages, the first reaction state containing a hydrotreating catalyst operated under effective hydrotreating conditions, and the second containing a hydrogenation catalyst has described herein operated under effective hydrogenation conditions as described above. Therefore, in such an embodiment, the hydrocarbon feedstream can be first contacted with a hydrotreating catalyst in the presence of a hydrogen-containing treat gas in a first reaction stage operated under effective hydrotreating conditions in order to reduce the sulfur content of the feedstream to within the above-described range. Thus, the term "hydrotreating" as used herein refers to processes wherein a hydrogen-containing treat gas is used in the presence of a suitable catalyst that is active for the removal of heteroatoms, such as sulfur, and nitrogen. Suitable hydrotreating catalysts for use in the present invention are any conventional hydrotreating catalyst and includes those which are comprised of at least one Group 8 metal, preferably Fe, Co and Ni, more preferably Co and/or Ni, and most preferably Ni; and at least one Group 6 metal, preferably Mo and W, more preferably Mo, on a high surface area support material, preferably alumina. Additionally or alternatively, more than one type of hydrotreating catalyst can be used in the same reaction vessel. The Group 8 metal may typically be present in an amount ranging from about 2 to 20 wt. %, preferably from about 4 to 12 wt. %. The Group 6 metal can typically be present in an amount ranging from about 5 to 50 wt. %, preferably from about 10 to 40 wt. %, and more preferably from about 20 to 30 wt. %. All metals weight percents are "on support" as described above.

Effective hydrotreating conditions may be considered to be those conditions that can effectively reduce the sulfur content of the feedstream (e.g., lube oil boiling range) to within the above-described ranges. Typical effective hydrotreating conditions can include temperatures ranging from about 150° C. to about 425° C., preferably about 200° C. to about 370° C., more preferably about 230° C. to about 350° C. Typical weight hourly space velocities ("WHSV") may range from about 0.1 to about 20 $hr^{-1}$, preferably from about 0.5 to about 5 $hr^{-1}$. Any effective pressure can be utilized, and pressures can typically range from about 4 to about 70 atmospheres (405 to 7093 kPa), preferably 10 to 40 atmospheres (1013 to 4053 kPa). In a particular embodiment, said effective hydrotreating conditions may be conditions effective at removing at least a portion of said organically bound sulfur contaminants and hydrogenating at least a portion of said aromatics, thus producing at least a reaction product (e.g., liquid lube oil boiling range product) having a lower concentration of aromatics and organically bound sulfur contaminants than the lube oil boiling range feedstream.

The contacting of the hydrocarbon feedstream with the hydrotreating catalyst may produce a reaction product comprising at least a vapor product and a liquid product. The vapor product may typically comprise gaseous reaction products, such as $H_2S$, and the liquid reaction product may typically comprise a liquid hydrocarbon having a reduced level of nitrogen and sulfur contaminants. The total reaction product can be passed directly into the second reaction stage, but it may be preferred that the gaseous and liquid reaction products be separated, and the liquid reaction product conducted to the second reaction stage. Thus, in one embodiment, the vapor product and the liquid product may be separated, and the liquid product may be conducted to the second reaction stage. The method of separating the vapor product from the liquid product can be accomplished by any means known to be effective at separating gaseous and liquid reaction products. For example, a stripping tower or reaction zone can be used to separate the vapor product from the liquid product (e.g., liquid lube oil boiling range product). The liquid product thus conducted to the second reaction stage can have a sulfur concentration within the range of about 500 wppm, particularly below about 300 wppm, or particularly below about 200 wppm or particularly below about 100 wppm.

In still other embodiments, the hydrogenation catalysts described herein can be used in integrated hydroprocessing methods. In addition to the hydrofinishing and/or aromatic hydrogenation/saturation processes involving the hydrogenation catalyst described herein, an integrated hydroprocessing method can also include various combinations of hydrotreating, hydrocracking, catalytic dewaxing (such as hydrodewaxing), and/or solvent dewaxing. The scheme of hydrotreating followed by hydrofinishing described above represents one type of integrated process flow. Another integrated processing example is to have a dewaxing step, either catalytic dewaxing or solvent dewaxing, followed by hydroprocessing with the hydrogenation catalysts described herein. Still another example is a process scheme involving hydrotreating, dewaxing (catalytic or solvent), and then hydroprocessing with the hydrogenation catalysts described herein. Yet another example is hydroprocessing with the hydrogenation catalysts described herein followed by dewaxing (catalytic or solvent). Alternatively, multiple hydrofinishing and/or aromatic hydrogenation steps can be employed with hydrotreatment, hydrocracking, or dewaxing steps. An example of such a process flow is hydrofinishing, dewaxing (catalytic or solvent), and then hydrofinishing again, where at least one of the hydrofinishing steps may use a hydrogenation catalysts described herein. For processes involving catalytic dewaxing, effective catalytic dewaxing conditions can include temperatures of from 150° C. to 400° C., preferably 250° C. to 350° C., pressures of from 791 to 20786 kPa (100 to 3000 psig), preferably 1480 to 17338 kPa (200 to 2500 psig), liquid hourly space velocities of from 0.1 to 10 $hr^{-1}$, preferably 0.1 to 5 $hr^{-1}$ and hydrogen treat gas rates from 45 to 1780 $m^3/m^3$ (250 to 10000 scf/B), preferably 89 to 890 $m^3/m^3$ (500 to 5000 scf/B). Any suitable dewaxing catalyst may be used.

In embodiments where the product of an aromatic saturation process will be a lubricant base oil, the input feed should also have suitable lubricant base oil properties. For example, an input feed intended for use as a Group I or Group II base oil can have a viscosity index (VI) of at least about 80, preferably at least about 90 or at least about 95. An input feed intended for use as a Group I+ base oil can have a VI of at least about 100, while an input feed intended for use as a Group II+ base oil can have a VI of at least 110. The viscosity of the input feed can be at least 2 cSt at 100° C., or at least 4 cSt at 100° C., or at least 6 cSt at 100° C.

VI. Further Embodiments

The invention can additionally or alternately include one or more of the following embodiments.

Embodiment 1

An aromatics hydrogenation process for a hydrocarbon feedstream comprising:

a) contacting a hydrocarbon feedstream comprising aromatics with a hydrogenation catalyst in the presence of a hydrogen-containing treat gas in a reaction stage operated under effective aromatics hydrogenation conditions to produce a reaction product with reduced aromatics content, wherein the hydrogenation catalyst comprises:

(i) an organosilica material support, which is a polymer comprising independent units of a monomer of Formula $[Z^1OZ^2OSiCH_2]_3$ (I), wherein each $Z^1$ and $Z^2$ independently represent a hydrogen atom, a $C_1$-$C_4$ alkyl group or a bond to a silicon atom of another monomer; and (ii) at least one catalyst metal selected from the group consisting of a Group 8 metal, a Group 9 metal, a Group 10 metal and a combination thereof.

Embodiment 2

The process of embodiment 1, wherein each $Z^1$ and $Z^2$ independently represent a hydrogen atom, a $C_1$-$C_2$ alkyl group or a bond to a silicon atom of another monomer.

Embodiment 3

The process of embodiment 1 or 2, wherein each $Z^1$ and $Z^2$ independently represent a hydrogen atom, ethyl or a bond to a silicon atom of another monomer.

Embodiment 4

The process of any one of the previous embodiments, wherein the organosilica material support further comprises at least one other monomer selected from the group consisting of:

(i) an independent unit of Formula $[Z^3OZ^4SiCH_2]_3$ (II), wherein each $Z^3$ represents a hydrogen atom, a $C_1$-$C_4$ alkyl group or a bond to a silicon atom of another monomer and each $Z^4$ represents a $C_1$-$C_6$ alkyl group;

(ii) an independent unit of Formula $Z^5OZ^6Z^7Z^8Si$ (III), wherein each $Z^5$ represents a hydrogen atom or a $C_1$-$C_4$ alkyl group or a bond to a silicon atom of another monomer; and $Z^6$, $Z^7$ and $Z^8$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group and an oxygen atom bonded to a silicon atom of another monomer;

(iii) an independent unit of Formula $Z^9Z^{10}Z^{11}Si$—R—$SiZ^9Z^{10}Z^{11}$ (IV), wherein each $Z^9$ independently represents a hydroxyl group, a $C_1$-$C_4$ alkoxy group or an oxygen bonded to a silicon atom of another comonomer; each $Z^{10}$ and $Z^{11}$ independently represent a hydroxyl group, a $C_1$-$C_4$ alkoxy group, a $C_1$-$C_4$ alkyl group or an oxygen bonded to a silicon atom of another monomer; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;

(iv) an independent unit of Formula $M^1(OZ^{12})_3$ (V), wherein $M^1$ represents a Group 13 metal and each $Z^{12}$ independently represents a hydrogen atom, a $C_1$-$C_6$ alkyl or a bond to a silicon atom of another monomer;

(v) an independent unit of Formula $(Z^{13}O)_2M^2$-O—Si $(OZ^{14})_3$ (VI), wherein $M^2$ represents a Group 13 metal and each $Z^{13}$ and each $Z^{14}$ independently represent a hydrogen atom, a $C_1$-$C_6$ alkyl group or a bond to a silicon atom of another monomer; and (vi) a combination thereof.

Embodiment 5

The process of embodiment 4, wherein at least one independent unit of Formula (II) is present, wherein each $Z^3$ represents a hydrogen atom, a $C_1$-$C_2$ alkyl group or a bond to a silicon atom of another siloxane monomer and each $Z^4$ represents a $C_1$-$C_2$ alkyl group.

Embodiment 6

The process of embodiment 4 or 5, wherein each $Z^3$ represents a hydrogen atom, ethyl or a bond to a silicon atom of another siloxane monomer and each $Z^4$ represents a methyl.

Embodiment 7

The process of any one of embodiments 4-6, wherein at least one independent unit of Formula (III) is present, wherein each $Z^5$ represents a hydrogen atom, a $C_1$-$C_2$ alkyl group or a bond to a silicon atom of another comonomer; and $Z^6$, $Z^7$ and $Z^8$ are each independently selected from the group consisting of a hydroxyl group, a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group and an oxygen bonded to a silicon atom of another monomer.

Embodiment 8

The process of embodiment 7, wherein $Z^6$, $Z^7$ and $Z^8$ are each independently selected from the group consisting of a hydroxyl group, a $C_1$-$C_2$ alkyl group, $C_1$-$C_2$ alkoxy group, and an oxygen bonded to a silicon atom of another monomer.

Embodiment 9

The process of embodiment 7, wherein each $Z^5$ represents a hydrogen atom, methyl, ethyl, or a bond to a silicon atom of another comonomer; and $Z^6$, $Z^7$ and $Z^8$ are each independently selected from the group consisting of a hydroxyl group, methyl, methoxy, ethoxy,

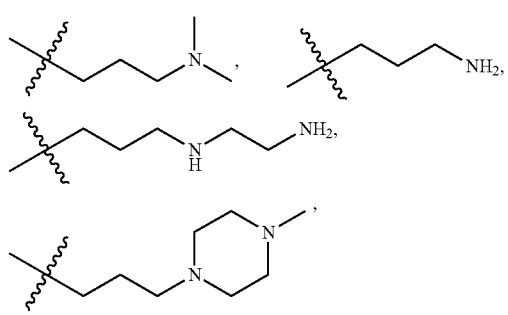

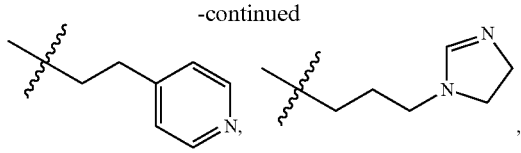

and an oxygen bonded to a silicon atom of another monomer.

Embodiment 10

The process of any one of embodiments 4-9, wherein at least one independent unit of Formula (IV) is present, wherein each $Z^9$ represents a hydroxyl group, a $C_1$-$C_2$ alkoxy group or an oxygen bonded to a silicon atom of another comonomer; each $Z^{10}$ and $Z^{11}$ independently represent a hydroxyl group, a $C_1$-$C_2$ alkoxy group, a $C_1$-$C_2$ alkyl group or an oxygen bonded to a silicon atom of another monomer; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

Embodiment 11

The process of embodiment 10, wherein each $Z^9$ represents a hydroxyl group, methoxy, ethoxy or an oxygen bonded to a silicon atom of another comonomer; each $Z^{10}$ and $Z^{11}$ independently represent a hydroxyl group, methoxy, ethoxy, methyl or an oxygen bonded to a silicon atom of another monomer; and R is selected from the group consisting of —CH$_2$—, —CH$_2$CH$_2$—, —HC=CH—,

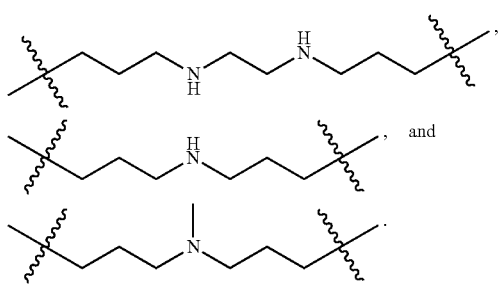

Embodiment 12

The process of any one of embodiments 4-11, wherein at least one independent unit of Formula (V) is present, wherein $M^1$ is Al or B and each $Z^{12}$ represents a hydrogen atom, a $C_1$-$C_4$ alkyl group or a bond to a silicon atom or another monomer.

Embodiment 13

The process of any one of embodiments 4-12, wherein at least one unit of Formula (VI) is present, wherein $M^2$ is Al or B and each $Z^{13}$ and each $Z^{14}$ independently represent a hydrogen atom, a $C_1$-$C_4$ alkyl group or a bond to a silicon atom of another monomer.

Embodiment 14

The process of any one of the previous embodiments, wherein the organosilica material support has a total surface area of about 500 m$^2$/g to about 2000 m$^2$/g.

Embodiment 15

The process of any one the previous embodiments, wherein the organosilica material support has a pore volume of about 0.5 cm$^3$/g to about 3.0 cm$^3$/g.

Embodiment 16

The process of any one of the previous embodiments, wherein the organosilica material support has an average pore diameter of 2.5 nm to 5 nm.

Embodiment 17

The process of any one of the previous embodiments, wherein the at least one catalyst metal is selected from the group consisting of Pt, Pd, Ir, Rh, Re, Ru, Os and a combination thereof.

Embodiment 18

The process of embodiment 17, wherein the at least one catalyst metal is selected from the group consisting of Pt, Pd, and a mixture thereof.

Embodiment 19

The process of any one of the previous embodiments, wherein the catalyst metal is present in an amount ranging from about 0.1 to about 2.0 wt. %.

Embodiment 20

The process of any one of the previous embodiments, wherein the hydrogenation catalyst further comprises a binder material selected from the group consisting of active and inactive materials, inorganic materials, clays, alumina, silica, silica-alumina, titania, zirconia, yttrium oxide, tantalum oxide, niobium oxide, activated carbon, ceramics, pumice, celite and a combination thereof.

Embodiment 21

The process of embodiment 20, wherein the binder material is selected from the group consisting of silica-alumina, alumina, titania, zirconia and activated carbon.

Embodiment 22

The process of any one of the previous embodiments, wherein the hydrocarbon feedstream is a hydrocarbon fluid, a diesel boiling range feedstream, a lube oil boiling range feedstream, a whole or reduced petroleum crude, atmospheric residua, vacuum residua, propane deasphalted residua, dewaxed oil, slack wax, raffinate, or a mixture thereof.

Embodiment 23

The process of any one of the previous embodiments, wherein the hydrocarbon feedstream contains up to 0.2 wt.

% of nitrogen, up to 3.0 wt. % of sulfur, and up to about 50 wt. % aromatics, all based on the hydrocarbon feedstream.

Embodiment 24

The process of any one of the previous embodiments, wherein the hydrocarbon feedstream has a sulfur content below about 100 wppm.

Embodiment 25

The process of any one of the previous embodiments, wherein the effective aromatics hydrogenation conditions comprise a temperature of about 350° C. or less.

Embodiment 26

A method of making a hydrogenation catalyst for aromatic hydrogenation, the method comprising.
a) providing an aqueous mixture that contains essentially no structure directing agent and/or porogen,
(b) adding at least one compound of Formula $[Z^{15}Z^{16}SiCH_2]_3$ (VII) into the aqueous mixture to form a solution, wherein each $Z^{15}$ represents a $C_1$-$C_4$ alkoxy group and each $Z^{16}$ represents a $C_1$-$C_4$ alkoxy group or a $C_1$-$C_4$ alkyl group;
(c) aging the solution to produce a pre-product;
(d) drying the pre-product to obtain an organosilica material support which is a polymer comprising independent units of a monomer of Formula $[Z^1OZ^2OSiCH_2]_3$ (I), wherein each $Z^1$ and $Z^2$ independently represent a hydrogen atom, a $C_1$-$C_4$ alkyl group or a bond to a silicon atom of another monomer; and
(e) impregnating the organosilica material support with at least one catalyst metal selected from the group consisting of a Group 8 metal, a Group 9 metal, a Group 10 metal and a combination thereof.

Embodiment 27

The method of embodiment 26, wherein each $Z^{15}$ represents a $C_1$-$C_2$ alkoxy group.

Embodiment 28

The method of embodiment 26 or 27, wherein each $Z^{16}$ represents a $C_1$-$C_4$ alkoxy group.

Embodiment 29

The method of any one of embodiments 26-28, wherein each $Z^{16}$ represents a $C_1$-$C_2$ alkoxy group.

Embodiment 30

The method of any one of embodiments 26-29, wherein the at least one compound of Formula (VII) is 1,1,3,3,5,5-hexaethoxy-1,3,5-trisilacyclohexane.

Embodiment 31

The method of any one of embodiments 26-30, wherein each $Z^1$ and $Z^2$ independently represent a hydrogen atom, a $C_1$-$C_2$ alkyl group or a bond to a silicon atom of another monomer.

Embodiment 32

The method of any one of embodiments 26-31, wherein each $Z^1$ and $Z^2$ independently represent a hydrogen atom, ethyl, or an oxygen bonded to a silicon atom of another monomer.

Embodiment 33

The method of any one of embodiments 26-32, further comprising grafting aluminum on the organosilica material support surface prior to impregnating the organosilica material support.

Embodiment 34

The method of any one of embodiments 26-33, further comprising adding to the aqueous mixture at least one compound selected from the group consisting of
(i) a further compound of Formula (VII);
(ii) a compound of Formula $Z^{17}OZ^{18}Z^{19}Z^{20}Si$ (VIII), wherein each $Z^{17}$ represents a $C_1$-$C_6$ alkyl group, and $Z^{18}$, $Z^{19}$ and $Z^{20}$ are each independently selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group;
(iii) compound of Formula $Z^{21}Z^{22}Z^{23}Si$—$R^1$—$Si$ $Z^{21}Z^{22}Z^{23}$ (IX), wherein each $Z^{21}$ independently represents a $C_1$-$C_4$ alkoxy group; each $Z^{22}$ and $Z^{23}$ independently represent a $C_1$-$C_4$ alkoxy group or a $C_1$-$C_4$ alkyl group; and $R^1$ is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
(iv) a source of a trivalent metal oxide; and
(v) a combination thereof.

Embodiment 35

The method of embodiment 34, wherein the at least one compound is a further compound of Formula (VII), wherein each $Z^{15}$ represents a $C_1$-$C_2$ alkoxy group and each $Z^{16}$ represent $C_1$-$C_2$ alkoxy group or a $C_1$-$C_2$ alkyl group.

Embodiment 36

The method of embodiment 35, wherein the compound of Formula (VII) is 1,3,5-trimethyl-1,3,5-triethoxy-1,3,5-trisilacyclohexane.

Embodiment 37

The method of any one of embodiments 34-36, wherein the at least one compound is a compound of Formula (VIII), wherein each $Z^{17}$ represents a $C_1$-$C_2$ alkyl group and $Z^{18}$, $Z^{19}$ and $Z^{20}$ each independently selected from the group consisting of a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

Embodiment 38

The method of embodiment 37, wherein the compound of Formula (VIII) is selected from the group consisting of tetraethyl orthosilicate, methyltriethoxysilane, (N,N-dimethylaminopropyl)trimethoxysilane, N-(2-aminoethyl)-3-aminopropyltriethoxysilane, 4-methyl-1-(3-triethoxysilylpropyl)-piperazine, 4-(2-(triethoxysily)ethyl)pyridine, 1-(3-(triethoxysilyl)propyl)-4,5-dihydro-1H-imidazole, and (3-aminopropyl)triethoxysilane.

Embodiment 39

The method of any one of embodiments 34-38, wherein the at least one compound is a compound of Formula (IX), wherein each $Z^{21}$ represents a $C_1$-$C_2$ alkoxy group; each $Z^{22}$ and $Z^{23}$ independently represent a $C_1$-$C_2$ alkoxy group, or a $C_1$-$C_2$ alkyl group; and $R^1$ is selected from the group consisting of a $C_1$-$C_4$ alkylene group, a $C_2$-$C_4$ alkenylene group, a $C_2$-$C_4$ alkynylene group, and a nitrogen-containing $C_4$-$C_{10}$ alkylene group.

Embodiment 40

The method of embodiment 39, wherein the compound of Formula (IX) is selected from the group consisting of 1,2-bis(methyldiethoxysilyl)-ethane, bis(triethoxysilyl)methane, 1,2-bis(triethoxysilyl)ethylene, N,N'-bis[(3-trimethoxysilyl)propyl]ethylenediamine, bis[(methyldiethoxysilyl)propyl]amine, and bis[(methyldimethoxysilyl)propyl]-N-methylamine.

Embodiment 41

The method of any one of embodiments 34-40, wherein the at least one compound is a source of trivalent metal oxide, wherein the source of trivalent metal oxide is at least one of:
a. a compound of Formula $M^3(OZ^{24})_3$ (X), wherein $M^3$ represents a Group 13 metal and each $Z^{24}$ independently represents a $C_1$-$C_6$ alkyl group; or
b. a compound of Formula $(Z^{25}O)_2M^4$-O—Si$(OZ^{26})_3$ (XI), wherein $M^4$ represents a Group 13 metal and each $Z^{25}$ and each $Z^{26}$ independently represent a $C_1$-$C_6$ alkyl group.

Embodiment 42

The method of embodiment 41, wherein the source of trivalent metal oxide is a compound of Formula (X), wherein $M^3$ is Al or B and each $Z^{24}$ represents a $C_1$-$C_4$ alkyl group.

Embodiment 43

The method of embodiment 41 or 42, wherein the source of trivalent metal oxide is a compound of Formula (XI), wherein $M^4$ is Al or B; and each $Z^{25}$ and each $Z^{26}$ independently represent a $C_1$-$C_4$ alkyl group.

Embodiment 44

The method of any one of embodiments 34-43, wherein the source of a trivalent metal oxide is selected from the group consisting of aluminum trimethoxide, aluminum triethoxide, aluminum isopropoxide, and aluminum-tri-sec-butoxide.

Embodiment 45

The method of any one of embodiments 26-44, wherein the aqueous mixture comprises a base and has a pH from about 8 to about 14.

Embodiment 46

The method of embodiment 45, wherein the base is ammonium hydroxide or a metal hydroxide.

Embodiment 47

The method of any one of embodiments 26-44, wherein the aqueous mixture comprises an acid and has a pH from about 0.01 to about 6.0.

Embodiment 48

The method of embodiment 47, wherein the acid is an inorganic acid.

Embodiment 49

The method of embodiment 48, wherein the inorganic acid is hydrochloric acid.

Embodiment 50

The method of any one of embodiments 26-49, wherein the solution is aged in step (c) for up to 144 hours at a temperature of about 50° C. to about 200° C.

Embodiment 51

The method of any one of embodiments 26-50, wherein the pre-product is dried at a temperature of about 70° C. to about 200° C.

Embodiment 52

The method of any one of embodiments 26-51 wherein the at least one catalyst metal is selected from the group consisting of Pt, Pd, Ir, Rh, Re, Ru, Os and a combination thereof.

Embodiment 53

The method of embodiment 52, wherein the at least one catalyst metal is selected from the group consisting of Pt, Pd, and a mixture thereof.

Embodiment 54

The method of any one of embodiments 26-53 further comprising adding a binder material, wherein the binder material selected from the group consisting of active and inactive materials, inorganic materials, clays, alumina, silica, silica-alumina, titania, zirconia, yttrium oxide, tantalum oxide, niobium oxide, activated carbon, ceramics, pumice, celite or a combination thereof.

Embodiment 55

The method of embodiment 54, wherein the binder material is selected from the group consisting of silica-alumina, alumina, silica, titania, and zirconia activated carbon.

Embodiment 56

A hydrogenation catalyst made according to the method of any one of embodiments 26-55.

Embodiment 57

A hydrogenation catalyst for aromatic hydrogenation comprising:
(i) an organosilica material support, which is a polymer comprising independent units of a monomer of Formula $[Z^1OZ^2OSiCH_2]_3$ (I), wherein each $Z^1$ and $Z^2$ independently represent a hydrogen atom, a $C_1$-$C_4$ alkyl group or a bond to a silicon atom of another monomer; and
(ii) at least one catalyst metal selected from the group consisting of a Group 8 metal, a Group 9 metal, a Group 10 metal and a combination thereof.

Embodiment 58

The hydrogenation catalyst of embodiment 57, wherein the organosilica material support further comprises at least one other monomer selected from the group consisting of:
(i) an independent unit of Formula $[Z^3OZ^4SiCH_2]_3$ (II), wherein each $Z^3$ represents a hydrogen atom, a $C_1$-$C_4$ alkyl group or a bond to a silicon atom of another monomer and each $Z^4$ represents a $C_1$-$C_6$ alkyl group;
(ii) an independent unit of Formula $Z^5OZ^6Z^7Z^8Si$ (III), wherein each $Z^5$ represents a hydrogen atom or a $C_1$-$C_4$ alkyl group or a bond to a silicon atom of another monomer; and $Z^6$, $Z^7$ and $Z^8$ are each independently selected from the group consisting of a hydroxyl group, a $C_1$-$C_4$ alkyl group, a $C_1$-$C_4$ alkoxy group, a nitrogen-containing $C_1$-$C_1°$ alkyl group, a nitrogen-containing heteroalkyl group, a nitrogen-containing optionally substituted heterocycloalkyl group and an oxygen atom bonded to a silicon atom of another monomer;
(iii) an independent unit of Formula $Z^9Z^{10}Z^{11}Si$—R—$SiZ^9Z^{10}Z^{11}$ (IV), wherein each $Z^9$ independently represents a hydroxyl group, a $C_1$-$C_4$ alkoxy group or an oxygen bonded to a silicon atom of another comonomer; each $Z^{10}$ and $Z^{11}$ independently represent a hydroxyl group, a $C_1$-$C_4$ alkoxy group, a $C_1$-$C_4$ alkyl group or an oxygen bonded to a silicon atom of another monomer; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
(iv) an independent unit of Formula $M^1(OZ^{12})_3$ (V), wherein $M^1$ represents a Group 13 metal and each $Z^{12}$ independently represents a hydrogen atom, a $C_1$-$C_6$ alkyl or a bond to a silicon atom of another monomer;
(v) an independent unit of Formula $(Z^{13}O)_2M^2$-O—Si$(OZ^{14})_3$ (VI), wherein $M^2$ represents a Group 13 metal and each $Z^{13}$ and each $Z^{14}$ independently represent a hydrogen atom, a $C_1$-$C_6$ alkyl group or a bond to a silicon atom of another monomer; and
(vi) a combination thereof.

Embodiment 59

The hydrogenation catalyst of embodiment 57 or 58, wherein aluminum is grafted on the organosilica material support surface.

EXAMPLES

General Methods

Small Angle X-ray Diffraction Analysis

X-ray powder diffraction (XRD) patterns were collected on a PANalytical X'pert diffractometer equipped with an accessory for low angle measurements. XRD analyses were recorded using the Cu Kα (=1.5405980 Å) line in the 2θ range from 0.5 to 10° with a step size of 0.0167° and a counting time of 1.2 s.

Solid-State (SS) NMR Measurements

The $^{29}Si$ MAS NMR spectra were recorded on a Varian InfinityPlus-400 spectrometer (operating at 9.4 T) and Varian InfinityPlus-500 (operating at 11.74 T), corresponding to $^{29}Si$ Larmor frequencies of 79.4 MHz and 99.2 MHz, respectively, with a 7.5 mm MAS probe heads using 5 kHz spinning, 4.0 µs 90° pulses, and at least 60 s recycle delay, with proton decoupling during data acquisition. The $^{29}Si$ chemical shifts are referenced with respect to an external tetramethyl silane ($\delta_{Si}$=0.0 ppm). The $^{13}C$ CPMAS NMR spectra were recorded on a Varian InfinityPlus-500 spectrometer corresponding to $^{13}C$ Larmor frequency of 125 MHz, with 1.6 mm MAS probe head using 40 kHz spinning, $^1H$—$^{13}C$ cross-polarization (CP) contact time of at least 1 ms, with a recycle delay of at least 1 s, with proton decoupling during data acquisition. The $^{13}C$ chemical shifts are referenced with respect to an external tetramethyl silane ($\delta_C$=0.0 ppm). The $^{27}Al$ MAS NMR spectra were recorded on a Varian InfinityPlus-500 corresponding to $^{27}Al$ Larmor frequency of 130.1 MHz using a 4 mm MAS probe head using 12 kHz spinning, with a π/12 radian pulse length, with proton decoupling during data acquisition, and a recycle delay of 0.3 s. The chemical shifts are referenced with respect to an external solution of $Al(H_2O)_6^{3+}$($\delta_{Al}$=0.0 ppm). All NMR spectra were recorded at room temperature using air for spinning.

Thermal Gravimetric Analysis (TGA)

Thermal stability results were recorded on Q5000 TGA. Ramp rate was 5° C./min, temperature range was from 25° C. to 800° C. All the samples were tested in both air and nitrogen.

$CO_2$ Adsorption

The work was done with a Quantchrom autosorb iQ2. All the samples were pre-treated at 120° C. in vacuum for 3 hours before collecting the $CO_2$ isotherm at different temperatures.

Nitrogen Porosimetry

The nitrogen adsorption/desorption analyses was performed with different instruments, e.g. TriStar 3000, TriStar II 3020 and Autosorb-1. All the samples were pre-treated at 120° C. in vacuum for 4 hours before collecting the $N_2$ isotherm. The analysis program calculated the experimental data and report BET surface area (total surface area), microporous surface area (S), total pore volume, pore volume for micropores, average pore diameter (or radius), etc.

Example 1—Catalyst Synthesis

Organosilica Material Support

A solution with 31.5 g of 30% $NH_4OH$ and 39.6 g deionized water (DI) water was made. The pH of the solution was 12.55. To the solution, 20 g of 1,1,3,3,5,5-hexaethoxy-1,3,5-trisilacyclohexane ($[(EtO)_2SiCH_2]_3$) was added, producing a mixture having the molar composition:

1.0[(Eto)$_2$SiCH$_2$]$_3$:21OH:270H$_2$O and stirred for 1 day at room temperature (20-25° C.). The solution was transferred to an autoclave and aged at 80° C.-90° C. for 1 day to produce a gel. The gel was dried at 80° C. in a vacuum to remove most of the water and then fully dried at 120° C. overnight (16-24 hours). This produced an organosilica material support as a clear solid, which was converted to white powder after grinding. No surface directing agent or porogen were used in this preparation.

Aluminum Grafting 0.141 g Al(O-i-Pr)$_3$ was dissolved into 30 ml anhydrous toluene and 6 g of the organosilica material support was added to form a solution. The solution was stirred at 110° C. for 1 day (16-24 hours). The solid was collected by centrifuge and then washed with toluene and methanol. The collected solid dried in an oven under vacuum at 120° C. to form an Al-organosilica material support.

Binder

The Al-organosilica material support was mixed and extruded with an alumina binder and water. Extrusion can be performed on wet or partially dried material. Suitable catalyst can be in the form of a powder, granules, or a molded product, with particle sizes fitting between 400 and 2 mesh size (Tyler scale). The extrudates were calcined at ~400° C. under an inert atmosphere (e.g. N$_2$) to prevent loss of surface area to obtain calcined extrudates.

Impregnation of Catalyst Metal

The calcined extrudates were impregnated with Pd and Pt salts by incipient wetness to create Catalyst 1. Metals salts can be added into the support+binder+water solution prior to extrusion. Metals can also be impregnated onto the support prior to mixing and extrusion. The impregnated material can be calcined under N$_2$ atmosphere to decompose the metals salts at temperatures resulting in good metals dispersion as defined by chemisorption. Calcination is not necessary if, for example, dispersion aids are used.

Nitrogen Adsorption/Desorption Analysis

Nitrogen adsorption/desorption analysis was performed on Catalyst 1 and the results are provided in Table 1.

TABLE 1

| Material | BET (m$^2$/g) | V (cc/g) | Pore diameter (nm) |
|---|---|---|---|
| Sample 1 | 869 | 0.85 | 4.0 |

Example 2—Aromatic Saturation Analysis

Aromatic saturation activity of Catalyst 1 tested on the petrochemical feed described below in Table 2 in a high-throughput experimental testing unit.

TABLE 2

| Property | Baton Rouge DWO Feed (H600N 65 ppm S) | Product Liquid after Aromatics Conversion |
|---|---|---|
| Total Aromatics (TA) by absorbance at 266 nm | 2.57 L/g-cm | 1.43 L/g-cm |
| Sulfur by X ray | 0.0073 mass % | |
| Nitrogen | <5 ppm | |
| Density | 0.86 g/ml | |
| American Petroleum Institute (API) Gravity | 30.37 | |

TABLE 2-continued

| Property | Baton Rouge DWO Feed (H600N 65 ppm S) | Product Liquid after Aromatics Conversion |
|---|---|---|
| Aromaticity | 3.6% | |
| Pour Point | −7° C. | |
| Cloud Point | 1° C. | |

For the testing, 0.08 g of Catalyst 1 sized to a 50/170 mesh was loaded into a batch reactor. After pressure testing with nitrogen, the catalyst was dried in nitrogen at 150° C. for 2 hours followed by reduction in 250 psig H$_2$ at 300° C. for 2 hours. The reactor was then cooled to room temperature and transferred to a glove box under a blanket of nitrogen. After opening the reactor under a blanket of nitrogen, approximately 3 cc of dewaxed oil was introduced to the batch reactor and the reactor was resealed. The aromatic saturation activity test was conducted for 12 hrs at 250° C. with 900 psig H$_2$.

The total aromatics were measured by UV-Vis adsorption test (using absorbance at 226 nm). The percentage of total aromatics converted was determined. The aromatic saturation experiment was run in triplicate to determine a standard deviation on the conversion and show statistical significance. Table 2 shows the results from batch testing for Catalyst 1. When normalized to the available metals surface area (SA), Catalyst 1 shows nearly equivalent aromatic saturation activity. The normalization was done using the estimated nanoparticle size from the 1/dispersion calculation.

UV-Vis experiments were done on a Perkin Elmer Lambda™ 850 spectrophotometer with Scantrag™ software by FTG. Samples were analyzed at room temperature (~15-25° C.) in a ~1 mm flow cell. If necessary, samples were combined with cyclohexane in solution to facilitate quantitative UV-Vis analysis.

What is claimed is:

1. An aromatics hydrogenation process for a hydrocarbon feedstream comprising:
    a) contacting a hydrocarbon feedstream comprising aromatics with a hydrogenation catalyst in the presence of a hydrogen-containing treat gas in a reaction stage operated under effective aromatics hydrogenation conditions to produce a reaction product with reduced aromatics content,
    wherein the hydrogenation catalyst comprises:
        (i) an organosilica material support, which is a polymer comprising independent units of a monomer of Formula [Z$^1$OZ$^2$OSiCH$_2$]$_3$ (I), wherein each Z$^1$ and Z$^2$ independently represent a hydrogen atom, a C$_1$-C$_4$ alkyl group or a bond to a silicon atom of another monomer, wherein the organosilica material support has an X-ray diffraction pattern with one peak between 1 and 3 degrees 2θ and no peaks in the range of from 3 to 20 degrees 2θ; and
        (ii) at least one catalyst metal selected from the group consisting of a Group 8 metal, a Group 9 metal, a Group 10 metal and a combination thereof.

2. The process of claim 1, wherein each Z$^1$ and Z$^2$ independently represent a hydrogen atom, a C$_1$-C$_2$ alkyl group or a bond to a silicon atom of another monomer.

3. The process of claim 2, wherein each Z$^1$ and Z$^2$ independently represent a hydrogen atom, ethyl or a bond to a silicon atom of another monomer.

4. The process of claim 1, wherein the organosilica material support further comprises at least one other monomer selected from the group consisting of:
(i) at least one independent unit of Formula [$Z^3OZ^4SiCH_2$]$_3$ (II), wherein each $Z^3$ represents a hydrogen atom, a $C_1$-$C_4$ alkyl group or a bond to a silicon atom of another monomer and each $Z^4$ represents a $C_1$-$C_6$ alkyl group;
(ii) at least one independent unit of Formula $Z^5OZ^6Z^7Z^8Si$ (III), wherein each $Z^5$ represents a hydrogen atom or a $C_1$-$C_4$ alkyl group or a bond to a silicon atom of another monomer; and $Z^6$, $Z^7$ and $Z^8$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group and an oxygen atom bonded to a silicon atom of another monomer;
(iii) at least one independent unit of Formula $Z^9Z^{10}Z^{11}Si$—R—$SiZ^9Z^{10}Z^{11}$ (IV), wherein each $Z^9$ independently represents a hydroxyl group, a $C_1$-$C_4$ alkoxy group or an oxygen bonded to a silicon atom of another comonomer; each $Z^{10}$ and $Z^{11}$ independently represent a hydroxyl group, a $C_1$-$C_4$ alkoxy group, a $C_1$-$C_4$ alkyl group or an oxygen bonded to a silicon atom of another monomer; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
(iv) at least one independent unit of Formula $M^1(OZ^{12})_3$ (V), wherein $M^1$ represents a Group 13 metal and each $Z^{12}$ independently represents a hydrogen atom, a $C_1$-$C_6$ alkyl or a bond to a silicon atom of another monomer;
(v) at least one independent unit of Formula $(Z^{13}O)_2M^2$-O—$Si(OZ^{14})_3$ (VI), wherein $M^2$ represents a Group 13 metal and each $Z^{13}$ and each $Z^{14}$ independently represent a hydrogen atom, a $C_1$-$C_6$ alkyl group or a bond to a silicon atom of another monomer; and
(vi) a combination thereof.

5. The process of claim 4, wherein at least one independent unit of Formula (II) is present, wherein each $Z^3$ represents a hydrogen atom, a $C_1$-$C_2$ alkyl group or a bond to a silicon atom of another siloxane monomer and each $Z^4$ represents a $C_1$-$C_2$ alkyl group.

6. The process of claim 5, wherein each $Z^3$ represents a hydrogen atom, ethyl or a bond to a silicon atom of another siloxane monomer and each $Z^4$ represents a methyl.

7. The process of claim 4, wherein at least one independent unit of Formula (III) is present, wherein each $Z^5$ represents a hydrogen atom, a $C_1$-$C_2$ alkyl group or a bond to a silicon atom of another comonomer; and $Z^6$, $Z^7$ and $Z^8$ are each independently selected from the group consisting of a hydroxyl group, a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group and an oxygen bonded to a silicon atom of another monomer.

8. The process of claim 7, wherein $Z^6$, $Z^7$ and $Z^8$ are each independently selected from the group consisting of a hydroxyl group, a $C_1$-$C_2$ alkyl group, $C_1$-$C_2$ alkoxy group, and an oxygen bonded to a silicon atom of another monomer.

9. The process of claim 7, wherein each $Z^5$ represents a hydrogen atom, methyl, ethyl, or a bond to a silicon atom of another comonomer; and $Z^6$, $Z^7$ and $Z^8$ are each independently selected from the group consisting of a hydroxyl group, methyl, methoxy, ethoxy,

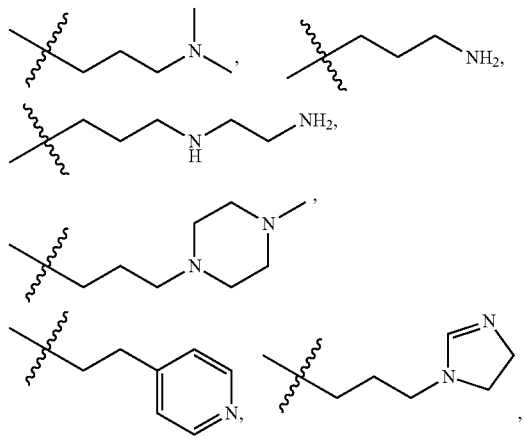

and an oxygen bonded to a silicon atom of another monomer.

10. The process of claim 4, wherein at least one independent unit of Formula (IV) is present, wherein each $Z^9$ represents a hydroxyl group, a $C_1$-$C_2$ alkoxy group or an oxygen bonded to a silicon atom of another comonomer; each $Z^{10}$ and $Z^{11}$ independently represent a hydroxyl group, a $C_1$-$C_2$ alkoxy group, a $C_1$-$C_2$ alkyl group or an oxygen bonded to a silicon atom of another monomer; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

11. The process of claim 10, wherein each $Z^9$ represents a hydroxyl group, methoxy, ethoxy or an oxygen bonded to a silicon atom of another comonomer; each $Z^{10}$ and $Z^{11}$ independently represent a hydroxyl group, methoxy, ethoxy, methyl or an oxygen bonded to a silicon atom of another monomer; and R is selected from the group consisting of

—$CH_2$—, —$CH_2CH_2$—, —HC=CH—,

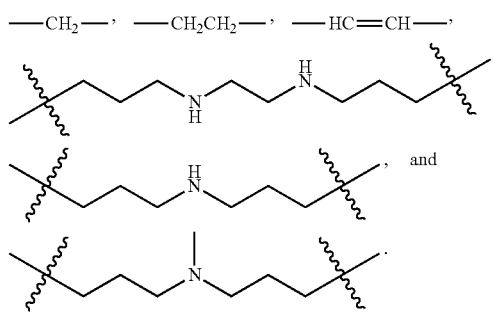

12. The process of claim 4, wherein at least one independent unit of Formula (V) is present, wherein $M^1$ is Al or B and each $Z^{12}$ represents a hydrogen atom, a $C_1$-$C_4$ alkyl group or a bond to a silicon atom or another monomer.

13. The process of claim 4, wherein at least one unit of Formula (VI) is present, wherein $M^2$ is Al or B and each $Z^{13}$ and each $Z^{14}$ independently represent a hydrogen atom, a $C_1$-$C_4$ alkyl group or a bond to a silicon atom of another monomer.

14. The process of claim 1, wherein the organosilica material support has a total surface area of about 500 m²/g to about 2000 m²/g.

15. The process of claim 1, wherein the organosilica material support has a pore volume of about 0.5 cm³/g to about 3.0 cm³/g.

16. The process of claim 1, wherein the organosilica material support has an average pore diameter of 2.5 nm to 5 nm.

17. The process of claim 1, wherein the at least one catalyst metal is selected from the group consisting of Pt, Pd, Ir, Rh, Re, Ru, Os and a combination thereof.

18. The process of claim 17, wherein the at least one catalyst metal is selected from the group consisting of Pt, Pd, and a mixture thereof.

19. The process of claim 1, wherein the catalyst metal is present in an amount ranging from about 0.1 to about 2.0 wt. %.

20. The process of claim 1, wherein the hydrogenation catalyst further comprises a binder material selected from the group consisting of active and inactive materials, inorganic materials, clays, alumina, silica, silica-alumina, titania, zirconia, yttrium oxide, tantalum oxide, niobium oxide, activated carbon, ceramics, pumice, celite and a combination thereof.

21. The process of claim 20, wherein the binder material is selected from the group consisting of silica-alumina, alumina, titania, zirconia and activated carbon.

22. The process of claim 1, wherein the hydrocarbon feedstream is a hydrocarbon fluid, a diesel boiling range feedstream, a lube oil boiling range feedstream, a whole or reduced petroleum crude, atmospheric residua, vacuum residua, propane deasphalted residua, dewaxed oil, slack wax, raffinate, or a mixture thereof.

23. The process of claim 1, wherein the hydrocarbon feedstream contains up to 0.2 wt. % of nitrogen, up to 3.0 wt. % of sulfur, and up to about 50 wt. % aromatics, all based on the hydrocarbon feedstream.

24. The process of claim 1, wherein the hydrocarbon feedstream has a sulfur content below about 100 wppm.

25. The process of claim 1, wherein the effective aromatics hydrogenation conditions comprise a temperature of about 350° C. or less.

* * * * *